United States Patent
Sugie et al.

(10) Patent No.: US 12,034,935 B2
(45) Date of Patent: Jul. 9, 2024

(54) RECEPTION APPARATUS, RECEPTION METHOD, AND IMAGE PROCESSING SYSTEM

(71) Applicant: SONY CORPORATION, Tokyo (JP)

(72) Inventors: Yuki Sugie, Tokyo (JP); Masaya Takemoto, Tokyo (JP); Masahito Yamane, Tokyo (JP)

(73) Assignee: SONY CORPORATION, Tokyo (JP)

( * ) Notice: Subject to any disclaimer, the term of this patent is extended or adjusted under 35 U.S.C. 154(b) by 489 days.

(21) Appl. No.: 17/276,732

(22) PCT Filed: Sep. 24, 2019

(86) PCT No.: PCT/JP2019/037184
§ 371 (c)(1),
(2) Date: Mar. 16, 2021

(87) PCT Pub. No.: WO2020/066972
PCT Pub. Date: Apr. 2, 2020

(65) Prior Publication Data
US 2022/0046248 A1  Feb. 10, 2022

(30) Foreign Application Priority Data

Sep. 28, 2018 (JP) ................. 2018-183269

(51) Int. Cl.
*H04N 19/136* (2014.01)
*G16H 30/20* (2018.01)
*H04N 7/01* (2006.01)
*H04N 19/103* (2014.01)
*H04N 19/167* (2014.01)

(52) U.S. Cl.
CPC ........... *H04N 19/136* (2014.11); *G16H 30/20* (2018.01); *H04N 7/0127* (2013.01); *H04N 19/103* (2014.11); *H04N 19/167* (2014.11)

(58) Field of Classification Search
CPC .. H04N 19/136; H04N 7/0127; H04N 19/103; H04N 19/167; H04N 19/186;
(Continued)

(56) References Cited

U.S. PATENT DOCUMENTS

2005/0238255 A1   10/2005  Niwa et al.
2007/0065032 A1*   3/2007  Hernandez ........... H04N 19/115
                                                375/E7.076
(Continued)

FOREIGN PATENT DOCUMENTS

CN          1666712 A    9/2005
CN        102103737 A    6/2011
(Continued)

OTHER PUBLICATIONS

International Search Report and Written Opinion of PCT Application No. PCT/JP2019/037184 dated Jan. 7, 2020, 11 pages of ISRWO.

*Primary Examiner* — Charlotte M Baker
(74) *Attorney, Agent, or Firm* — CHIP LAW GROUP

(57) ABSTRACT

The present disclosure relates to a reception apparatus, a reception method, and an image processing system that can suppress a reduction in resolution of an image that a surgery operator wants to see at a high resolution while responding to an increase in the number of connections of medical equipment that supply images. In the previous stage of a transmission path such as PCIe, images are acquired from a plurality of pieces of medical equipment, a compression method is selected for each type of image, and the image is compressed and output to the transmission path. Therefore, among YCbCr signals, e.g., of a CT image or an X image, an image that does not require CbCr signals is compressed as the Y signal only, and an image that requires a high-resolution image such as an operative field image is transmitted without being compressed. Therefore, it is possible to (Continued)

| TRANSMISSION FORMAT | PCIe BAND | GPU SIGNAL PROCESSING |
|---|---|---|
| 16-bit PACKING FORMAT | NG | NA |
| HIGH COMPRESSION PACKING FORMAT | OK | Poor Unpack IS HIGH LOAD |
| HETERO-PACKING FORMAT | OK | Rich | suppress compression of the band of a transmission path such as PCIe. The present disclosure can be applied to an intra-hospital image processing system.

16 Claims, 15 Drawing Sheets

(58) Field of Classification Search
CPC ...... H04N 7/18; H04N 19/156; H04N 21/436; G16H 30/20; G16H 10/60; G16H 20/40; G16H 40/67; A61B 5/00
USPC .......................................................... 382/128
See application file for complete search history.

(56) References Cited

U.S. PATENT DOCUMENTS

| 2007/0140538 | A1* | 6/2007 | Doran | G16H 30/40 |
| | | | | 382/128 |
| 2011/0141261 | A1 | 6/2011 | Oshima et al. | |
| 2011/0176054 | A1* | 7/2011 | Omae | H04N 19/164 |
| | | | | 348/E11.006 |
| 2012/0081385 | A1 | 4/2012 | Cote et al. | |
| 2018/0020232 | A1* | 1/2018 | Saeedi | H04N 19/186 |

FOREIGN PATENT DOCUMENTS

| CN | 102547301 A | 7/2012 |
| EP | 2341385 A1 | 7/2011 |
| EP | 2622867 A1 | 8/2013 |
| JP | 2005-288157 A | 10/2005 |
| JP | 2011-130074 A | 6/2011 |
| JP | 2015-019679 A | 2/2015 |
| JP | 2018-112716 A | 7/2018 |
| KR | 10-2011-0068863 A | 6/2011 |
| KR | 10-2012-0107041 A | 9/2012 |
| WO | 2012/047425 A1 | 4/2012 |

* cited by examiner

FIG. 9

| TRANSMISSION FORMAT | PCIe BAND | GPU SIGNAL PROCESSING |
|---|---|---|
| 16-bit PACKING FORMAT | NG | NA |
| HIGH COMPRESSION PACKING FORMAT | OK | Poor Unpack IS HIGH LOAD |
| HETERO-PACKING FORMAT | OK | Rich |

RECEPTION APPARATUS, RECEPTION METHOD, AND IMAGE PROCESSING SYSTEM

CROSS REFERENCE TO RELATED APPLICATIONS

This application is a U.S. National Phase of International Patent Application No. PCT/JP2019/037184 filed on Sep. 24, 2019, which claims priority benefit of Japanese Patent Application No. JP 2018-183269 filed in the Japan Patent Office on Sep. 28, 2018. Each of the above-referenced applications is hereby incorporated herein by reference in its entirety.

TECHNICAL FIELD

The present disclosure relates to a reception apparatus, a reception method, and an image processing system, and particularly to a reception apparatus, a reception method, and an image processing system that can suppress a reduction in resolution of an image that a surgery operator wants to see at a high resolution while responding to an increase in the number of connections of medical equipment that supply images.

BACKGROUND ART

In recent years, medical images from a plurality of medical equipment has been combined into a single display image and the plurality of medical images is simultaneously displayed on a display apparatus such that various information can be read simultaneously to improve surgical efficiency and reduce the surgery room occupancy by the display apparatus.

For example, a technique for combining medical images of a plurality of medical equipment into a single display image and displaying it on a display apparatus (HMD) is disclosed (see Patent Document 1).

CITATION LIST

Patent Document

Patent Document 1: Japanese Patent Application Laid-Open No. 2015-19679

SUMMARY OF THE INVENTION

Problems to be Solved by the Invention

However, in order to combine medical images from a plurality of medical equipment into a single display image and simultaneously display the plurality of medical images on the display apparatus, it is necessary to transmit and receive the plurality of medical images from the plurality of medical equipment, and therefore the data transmission band is compressed in some cases.

Thus, a conceivable way would be to secure the data transmission band by reducing the number of connected medical equipment, but reducing the number of connected medical equipment reduces the number of images that can be displayed.

Furthermore, a conceivable way would be a method of uniformly reducing the data capacity output from the medical equipment, but when the data capacity is uniformly reduced, the resolution of the image that the surgery operator wants to see as a high-resolution image is reduced.

The present disclosure has been made in view of such a situation, and particularly suppresses a reduction in resolution of an image that a surgery operator wants to see at a high resolution while responding to an increase in the number of connections of medical equipment that supply images.

Solutions to Problems

The reception apparatus according to a first aspect of the present disclosure is a reception apparatus including: an acquisition unit that acquires an image from a plurality of pieces of equipment; and a plurality of compression units that compresses the image acquired by the acquisition unit by selecting a compression method for each type of the image.

The reception method according to a first aspect of the present disclosure is a reception method including: acquisition processing of acquiring an image from a plurality of pieces of equipment; and compression processing of compressing the image acquired by the acquisition processing by selecting a compression method for each type of the image.

According to the first aspect of the present disclosure, images are acquired from a plurality of pieces of equipment, and the acquired images are compressed by selecting a compression method for each type of the image.

The image processing system according to a second aspect of the present disclosure is an image processing system including: an image server that stores an image from a plurality of pieces of equipment; and a reception apparatus that acquires an image from the image server, outputs the image to a display unit, and causes the display unit to display the image, in which the image server stores an image from the plurality of pieces of equipment and includes an output unit that outputs the stored image to the reception apparatus, and the reception apparatus includes an acquisition unit that acquires the image from the plurality of pieces of equipment from the image server and a plurality of compression units that compresses the image acquired by the acquisition unit by selecting a compression method for each type of the image.

According to the second aspect of the present disclosure, the image server stores images from the plurality of pieces of equipment, the stored images are output to the reception apparatus, the reception apparatus causes the plurality of images from the plurality of pieces of equipment to be acquired from the image server, and the acquired image is compressed by selecting a compression method for each type of the image.

Effects of the Invention

According to one aspect of the present disclosure, it is particularly possible to suppress a reduction in resolution of an image that a surgery operator wants to see at a high resolution while responding to an increase in the number of connections of medical equipment that supply images.

BRIEF DESCRIPTION OF DRAWINGS

FIG. 9 is a diagram explaining an example of switching a bit packing format according to a processing load of a GPU.

MODE FOR CARRYING OUT THE INVENTION

Figure 1:
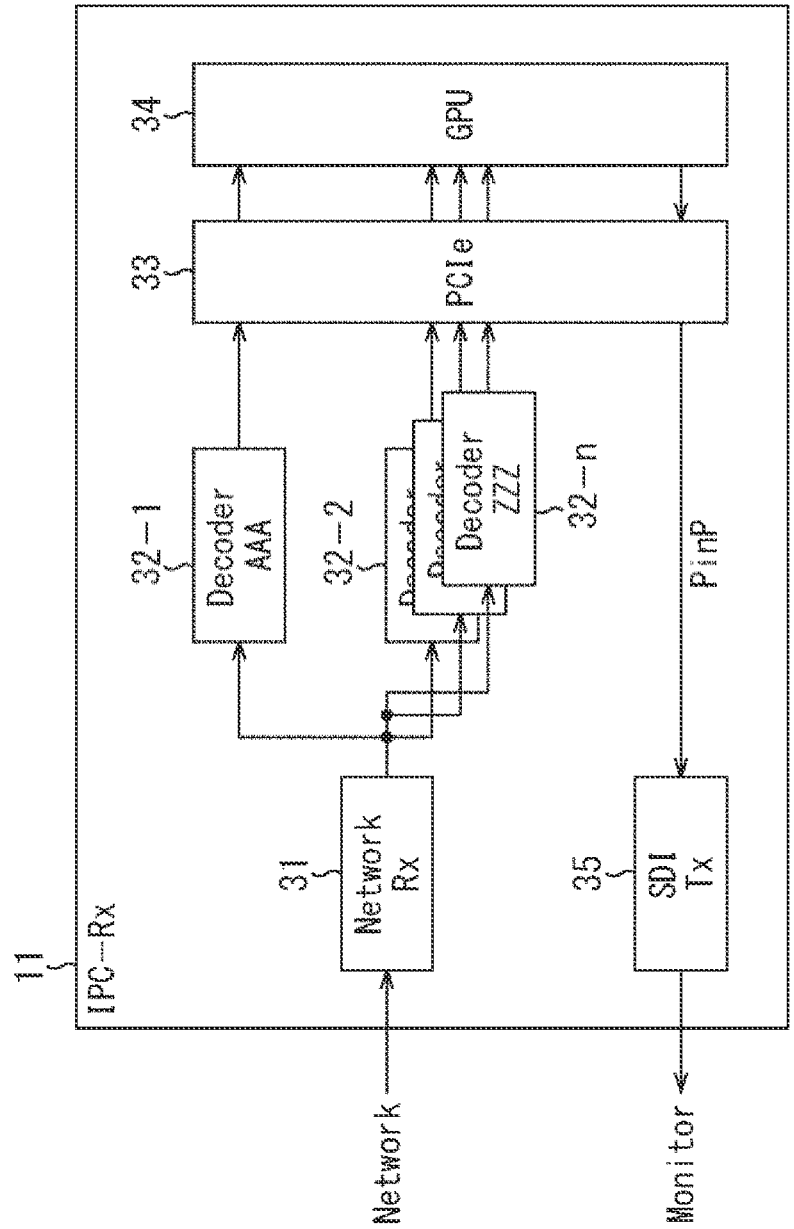
FIG. 1 is a diagram explaining an overview of an IP converter reception apparatus.

Preferred embodiments of the present disclosure will be described in detail below with reference to the accompanying drawings. Note that, in this description and the drawings, configuration elements that have substantially the same function and configuration are denoted with the same reference numerals, and repeated explanation is omitted.

Aspects for carrying out the present technology are described below. The description is provided in the order set forth below.

1. Overview of the IP converter reception apparatus (IPC)
2. Configuration example of the intra-hospital image processing system of the present disclosure
3. Configuration example of the first embodiment of the IP converter reception apparatus
4. Configuration example of the second embodiment of the IP converter reception apparatus
5. Configuration example of the third embodiment of the IP converter reception apparatus
6. Example of execution by software
7. Application example 1. Overview of the IP Converter Reception Apparatus (IPC)

The overview of an interlace protocol (IP) converter reception apparatus (IPC) will be described with reference to FIG. 1.

FIG. 1 shows a configuration example of an IP converter reception apparatus (IPC-Rx) 11.

The IP converter reception apparatus (IPC-Rx) 11 receives a plurality of IP-packetized images, combines them into a single image (PinP image), converts it into an image signal, and outputs the image signal to a monitor to cause the monitor to display the image.

In the present specification, the IP converter reception apparatus (IPC-Rx) 11 combines an image preliminarily captured in a hospital or an image during surgery into a single image for presentation to the surgery operator, converts it into a predetermined image signal, and outputs the image signal to a monitor to cause the monitor to display the image.

More specifically, the IP converter reception apparatus (IPC-Rx) 11 includes an input unit (Network Rx) 31, decoders (Decoder) 32-1 to 32-n, an expansion bus (peripheral component interconnect express (PCIe)) 33, a graphics processing unit (GPU) 34, and an output unit (serial digital interface (SDI)-Tx) 35.

The input unit 31 is a serial interface, and receives, in addition to IP-packetized images such as medical images preliminarily captured in a hospital, an input of a plurality of types of stream images such as images currently captured during surgery, via a network (Network), and outputs the images to the decoders 32-1 to 32-n that decode the stream images according to the type.

The decoders (Decoder AAA to Decoder ZZZ) 32-1 to 32-n are decoders that decode the stream images according to the type of encoding, and output the decoded stream images to the expansion bus (PCIe) 33. Note that "AAA" to "ZZZ" in "Decoder AAA" to "Decoder ZZZ" in the drawing indicate that they are decoders corresponding to different types of encoding.

The expansion bus (PCIe) 33 is a data transmission path between the decoders 32-1 to 32-n and the GPU 34 and between the GPU 34 and the output unit (SDI-Tx) 35, outputs a plurality of decoded stream images to the GPU 34, and outputs a single picture in picture (PinP) image generated by the GPU 34 to the output unit (SDI-Tx) 35.

The GPU 34 generates a single picture in picture (PinP) image by combining a plurality of images and outputs the PinP image to the expansion bus 33.

The output unit (SDI-Tx) 35 converts the single PinP image into a predetermined image signal, outputs the image signal to a monitor (Monitor) provided in a surgery room and including a display such as liquid crystal display (LCD) and organic electro luminescence (EL), and causes the monitor to display the image.

With such a configuration, first, in addition to images such as CT images and MRI images, an input of a plurality of types of IP-packetized stream images such as operative field images, endoscopic images, and laparoscopic images currently captured is received. Then, the input stream images are decoded for each type, and the plurality of stream images is combined to generate a single PinP image. The image is converted into a predetermined image signal such as 3G-SDI, and is supplied to the monitor provided in a surgery room where the image signal is displayed as a single image.

By the way, the types of images input to the IP converter reception apparatus 11 tend to increase year by year, and there has been a possibility that the band in the expansion bus (PCIe) 33 is compressed and a delay may occur in the display of the PinP image displayed on the monitor.

At present, the occurrence of delay is avoided by limiting the number of input images input to the IP converter reception apparatus 11 and reducing the size of the input images (reducing the resolution).

However, the method of limiting the number of input images input to the IP converter reception apparatus 11 and reducing the size of the input images (reducing the resolution) can be said to be a method that recedes against measures to multimodality (making multiple different medical image data centrally manageable and viewable) and the progress of the image processing technology that increases the resolution.

Therefore, the IP converter reception apparatus of the present disclosure changes a compression rate depending on the type of image so that the compression rate is high for the types of images that have little effect even when the image quality is sacrificed so as to suppress a reduction in resolution of the image that the surgery operator wants to see at a high resolution while accepting an input of a greater number of images.

2. Configuration Example of the Intra-Hospital Image Processing System of the Present Disclosure Next, a configuration example of the intra-hospital image processing system of the present disclosure will be described with reference to FIG. 2.

Figure 2:
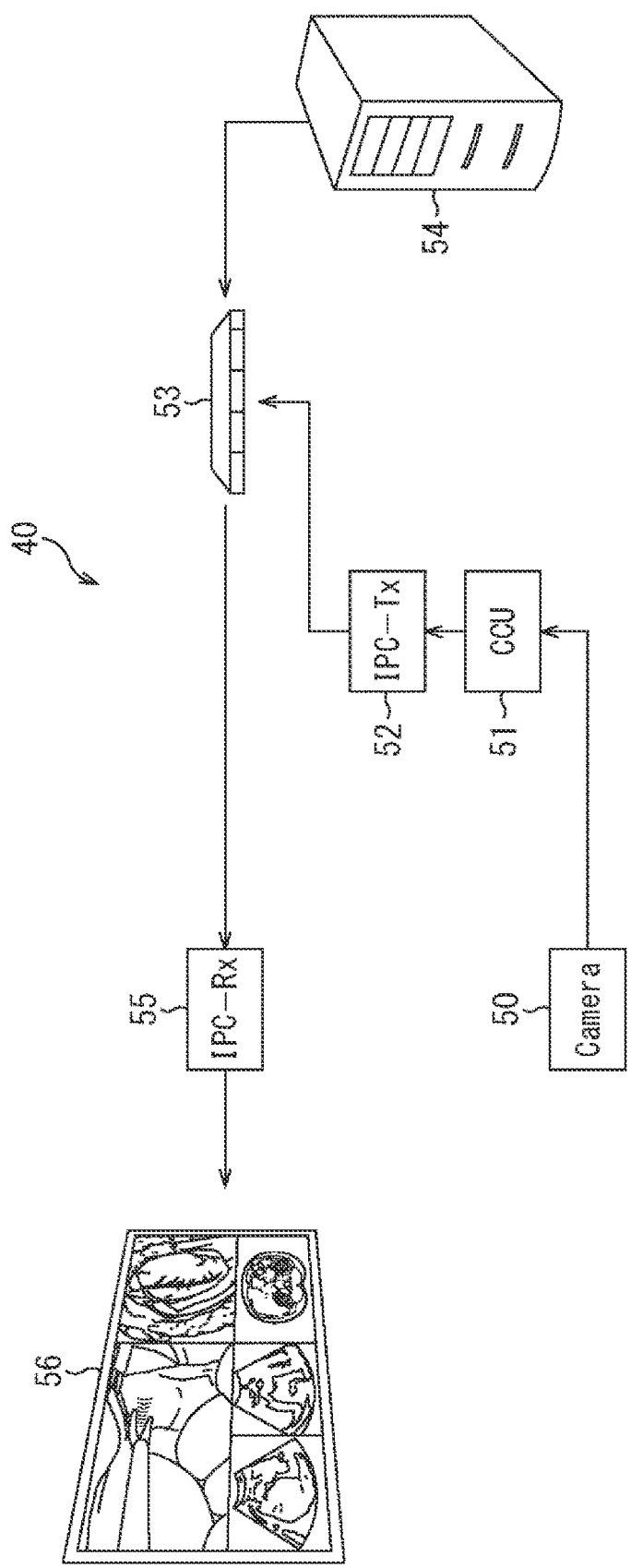
FIG. 2 is a diagram explaining a configuration example of an intra-hospital image processing system of the present disclosure.

An intra-hospital image processing system 40 of FIG. 2 records and manages images in a hospital, and combines the recorded and managed images and images during surgery into a single image and presents the image to the surgery operator.

More specifically, the intra-hospital image processing system 40 includes a camera (Camera) 50, a camera control unit (CCU) 51, an IP converter transmission apparatus (IPC-Tx) 52, a hub 53, an image management server 54, an IP converter reception apparatus (IPC-Rx) 55, and a monitor 56.

The camera 50 is an imaging apparatus installed in a surgery room, and is controlled by the CCU 51 and captures, for example, an operative field image, an endoscopic image, a laparoscopic image, and the like as stream images, and outputs the stream image to the camera control unit (CCU) 51. The camera 50 outputs the captured stream image to the camera control unit (CCU) 51 as an image signal such as YCC/422/10 bit of 3 Gbps-serial digital interface (3G-SDI). Note that the scheme of the image signal is not limited to YCC/422/10 bit of 3G-SDI, but may be other various schemes.

The camera control unit (CCU) 51 controls the operation of the camera 50 and outputs the image signal of the stream image captured by the camera 50 to the IP converter transmission apparatus (IPC-Tx) 52.

Note that although there is only one camera 50 in FIG. 2, a plurality of cameras 50 may be provided. Furthermore, instead of the camera 50 and the camera control unit (CCU) 51, medical equipment capable of supplying medical images such as computed tomography (CT) images and magnetic resonance imaging (MRI) images may be connected so that medical images can be supplied.

The IP converter transmission apparatus (IPC-Tx) 52 encodes the image signal constituting the stream image into a stream scheme such as low latency video codec (LLVC) and outputs it as an IP-packetized network signal to the IP converter reception apparatus 55 or the image management server 54 via the hub 53.

The type of encoding of the stream image may be other than LLVC, and may be, for example, MPEG-4 Part 10 Advanced Video Coding (H264), Joint Photographic Experts Group 2000 (JPEG2000), Differential Pulse Code Modulation (DPCM), and the like.

The image management server 54 is, for example, an operation room (OR) server provided in the hospital, acquires and stores various types of images (so-called multimodality images) such as a computed tomography (CT) image, a magnetic resonance imaging (MRI) image, and an X-ray image, which are preliminarily captured in the hospital, via the hub 53, and outputs the images to the IP converter reception apparatus 55 via the hub 53 as needed.

The IP converter reception apparatus 55 processes the images captured by the camera 50 via the hub 53 and various images supplied from the image management server 54 into a single image, outputs the image as the image signal to the monitor 56, and causes the monitor 56 to display the image.

With such a configuration, the IP converter reception apparatus 55 presents necessary information to the surgery operator by combining CT images, MRI images, X images, and the like preliminarily captured in the hospital as well as operative field images, endoscopic images, laparoscopic images, and the like into a single image and displaying it on the monitor with respect to the surgery operator. Here, LLVC and H264 are visually lossless compression methods, and JPEG2000 and DPCM are lossless compression methods. Therefore, in a case of combining into a single PinP image, for example, for operative field images, endoscopic images, laparoscopic images, and the like that are combined as a main image, the encoding method may be JPEG2000 or DPCM, and for images that are sub-images, the encoding method may be LLVC or H264.

3. Configuration Example of the First Embodiment of the IP Converter Reception Apparatus Next, a configuration example of the first embodiment of the IP converter reception apparatus (IPC-Rx) 55 of FIG. 2 will be described with reference to FIG. 3.

More specifically, the IP converter reception apparatus (IPC-Rx) 55 includes an input unit (Network Rx) 71, decoders (Decoder AAA to Decoder ZZZ) 72-1 to 72-n, bit packing units (BitPack) 73-1 to 73-n, a bit packing control unit (PackingCtrl) 74, a table (Table) 75, an expansion bus (peripheral component interconnect express (PCIe)) 76, a graphics processing unit (GPU) 77, and an output unit (serial digital interface (SDI) 78.

The input unit (Network Rx) 71 is an interface that accepts the input of a plurality of stream images such as operative field images, endoscopic images, and laparoscopic images that are currently captured in addition to images such as IP-packetized CT images, MRI images, and X-ray images, and outputs a corresponding stream image to the decoders 72-1 to 72-n that perform decoding by the corresponding type of decoding method according to the type of image.

The decoders (Decoder AAA to Decoder ZZZ) 72-1 to 72-n are decoders each decoding the stream images for each type of encoding and outputting the decoded stream images to the respective bit packing units 73-1 to 73-n. Note that "AAA" to "ZZZ" in "Decoder AAA" to "Decoder ZZZ" in the drawing indicate that they are decoders corresponding to different types of encoding.

The bit packing units (BitPack) 73-1 to 73-n, on the basis of information object definition (IOD) data of ancillary data (for example, digital imaging and communications in medicine (DICOM)) in the image signal of the decoded stream image, extracts and recognizes the type of the image signal, and supplies the type of the image signal to the bit packing control unit (PackingCtrl) 74.

The bit packing units (BitPack) 73-1 to 73-n compress the image signal by bit packing by a bit packing method specified by the bit packing control unit (PackingCtrl) 74 according to the type of the image signal, and outputs the image signal to the GPU 77 via the expansion bus (PCIe) 76.

The bit packing control unit (PackingCtrl) 74 accesses the table (Table) 75 that stores information of the bit packing method according to the type of image signal supplied from each of the bit packing units (BitPack) 73-1 to 73-n, reads the information of the bit packing method according to the type of the image signal, and outputs it to each of the bit packing units (BitPack) 73-1 to 73-*n*.

The expansion bus (peripheral component interconnect express (PCIe)) 76 is a data transmission path from the bit packing units (BitPack) 73-1 to 73-*n* to the GPU 77 and a transmission path from the GPU 77 to the output unit (serial digital interface (SDI) 78, outputs a plurality of decoded stream images to the GPU 77, and outputs a single PinP image generated by the GPU 34 to the output unit (SDI-Tx) 78.

The graphics processing unit (GPU) 77 generates a single picture in picture (PinP) image by image processing that combines a plurality of images transmitted via the expansion bus (peripheral component interconnect express (PCIe)) 76, and outputs the image to the expansion bus 76.

The output unit (serial digital interface (SDI)-Tx) 78 is a serial interface that converts the PinP image into a predetermined image signal, outputs the image signal to a monitor (Monitor) 56 provided in a surgery room and including a display such as liquid crystal display (LCD) and organic electro luminescence (EL), and causes the monitor to display the image.

That is, with the above configuration, for example, in a case where the type of the supplied image signal is a CT image, the PinP image finally generated is a black and white image. Therefore, a bit packing method that applies compression so that a Y signal is 10 bits and Cb and Cr signals are 0 bits in the image signal is selected. Furthermore, since the operative field image, the endoscopic image, the laparoscopic image, and the like are images desired by the surgery operator to be high-resolution images, a bit packing method that puts them in an uncompressed state is selected.

In this way, the bit packing method is selected so as to switch between the bit depth of the Y signal and the bit depth of the Cb and Cr signals according to the type of the image signal. Therefore, it is possible to reduce the compression of the band of the expansion bus (PCIe) 76 by reducing the data amount and compressing the types of images that have no effect even when the image quality is reduced.

As a result, it is possible to suppress a reduction in resolution of an image that a surgery operator wants to see at a high resolution while responding to an increase in the number of connections of medical equipment that supply images.

Figure 3:
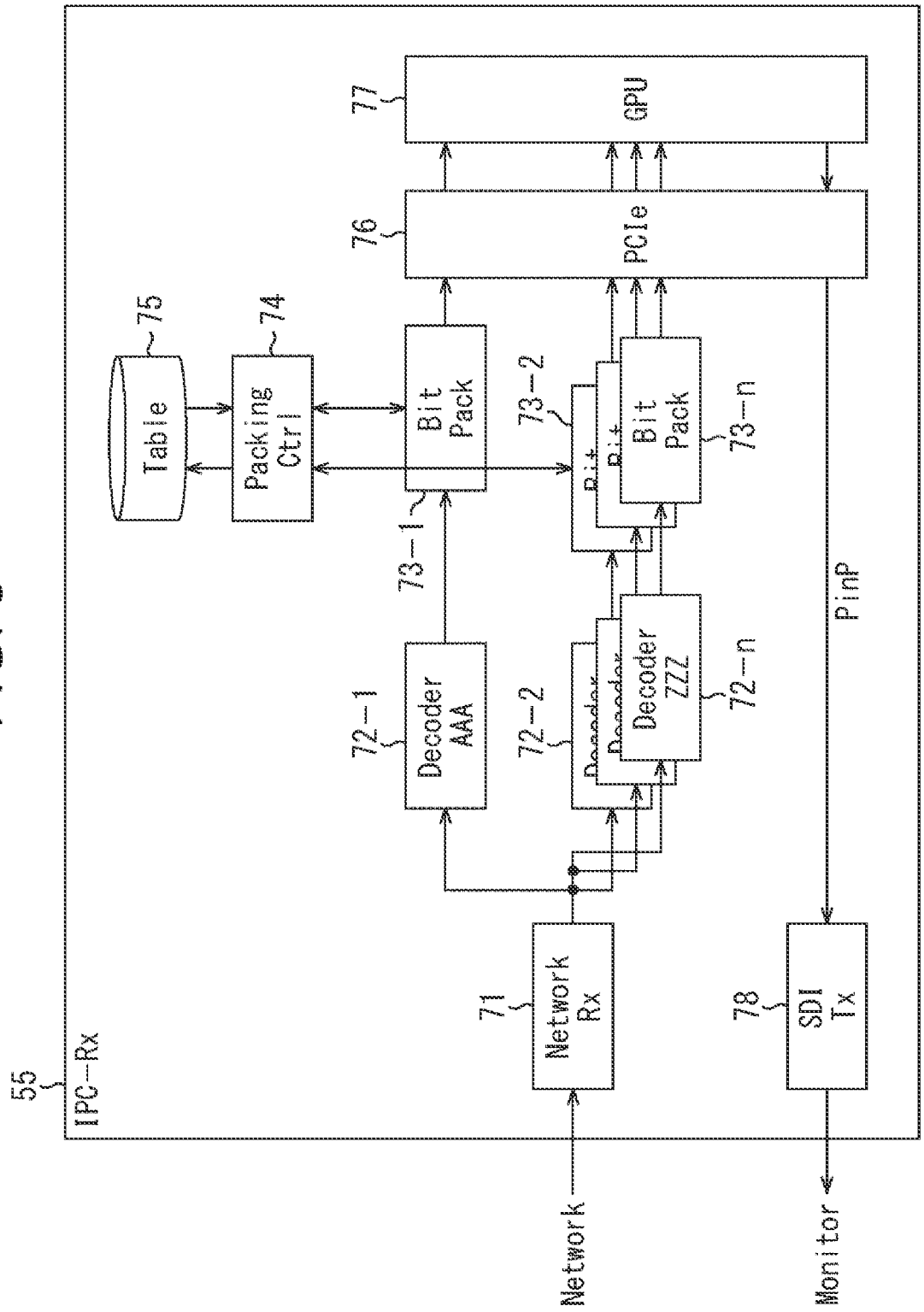
FIG. 3 is a diagram explaining a configuration example of a first embodiment of the IP converter reception apparatus.

<Display Control Processing by the IP Converter Reception Apparatus in FIG. 3>

Figure 4:
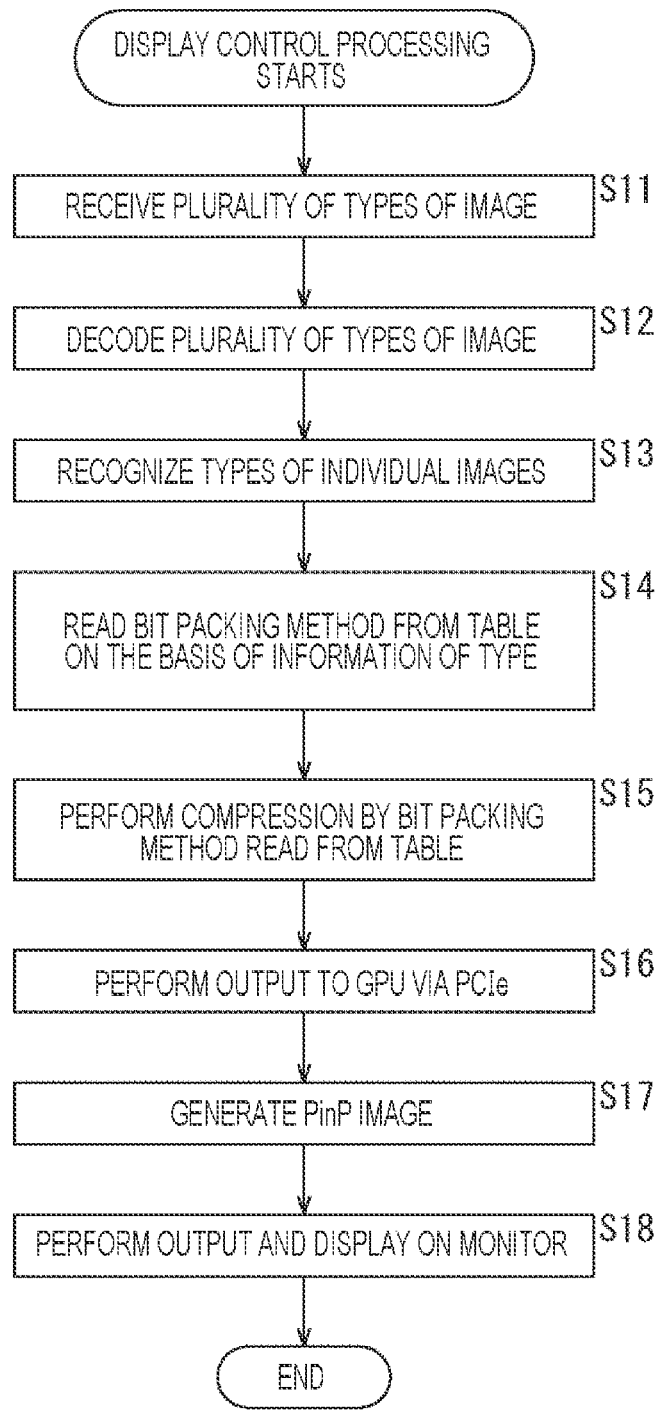
FIG. 4 is a flowchart explaining display control processing by the IP converter reception apparatus of FIG. 3.

Next, the display control processing by the IP converter reception apparatus 55 of FIG. 3 will be described with reference to the flowchart of FIG. 4.

In step S11, the input unit (Network Rx) 71 accepts an input of a plurality of types of stream images and outputs them to the decoders 72-1 to 72-*n* that decode the corresponding stream images according to the type of encoding. The plurality of types of stream images includes, for example, images such as IP-packetized CT images, and MRI images supplied from the image management server 54 via the hub 53, and operative field images, endoscopic images, laparoscopic images, and the like currently captured by the camera 50 via the CCU 51, the IP converter (IPC-Tx) 52, and the hub 53.

In step S12, the decoders (Decoder) 72-1 to 72-*n* decode the types of stream images for each type of encoding, and output the decoded stream images to the respective bit packing units 73-1 to 73-*n*.

In step S13, the bit packing units (BitPack) 73-1 to 73-*n* each extract and recognize information of the types of individual image signals on the basis of the ancillary data (DICOM IOD data) in the image signal of the decoded stream images, and supplies the information to the bit packing control unit (PackingCtrl) 74.

In step S14, the bit packing control unit (PackingCtrl) 74 accesses the table (Table) 75, reads the information of the bit packing method according to the type of the image signal supplied from each of the bit packing units (BitPack) 73-1 to 73-*n*, and outputs the information to each of the bit packing units (BitPack) 73-1 to 73-*n*.

In step S15, the bit packing units (BitPack) 73-1 to 73-*n* bit-pack (compress) the image signal by the bit packing method according to the type of the image signal supplied from the bit packing control unit (PackingCtrl) 74.

In step S16, the bit packing units (BitPack) 73-1 to 73-*n* output the bit-packed image signal to the GPU 77 via the expansion bus (PCIe) 76.

In step S17, the graphics processing unit (GPU) 77 generates a single picture in picture (PinP) image by image processing that combines a plurality of images, and outputs the image to the output unit 78 via the expansion bus 76.

In step S18, the output unit (serial digital interface (SDI)) 78 outputs the image signal of the PinP image to the monitor 56 provided in the surgery room and including the display and causes the monitor to display the image.

By the above processing, in the previous stage of the expansion bus (PCIe) 76, the bit packing method is switched according to the type of the image signal. For the image signal that has little effect even when the image quality is reduced due to a reduction in data amount of the image signal by compression, the data amount is reduced (compressed) so that the compression of the band of the expansion bus (PCIe) 76 can be suppressed.

As a result, it is possible to suppress a reduction in resolution of an image that a surgery operator wants to see at a high resolution while responding to an increase in the number of connections of medical equipment that supply images.

Note that the bit packing method may be switched by a method other than the method of changing the bit depth of the Y signal and the Cb and Cr signals. For example, according to the type of the image signal, the bit punking method may be switched to switch the format of components such as YC444, YC422, and YC420.

In this way, according to the type of image signal, the bit packing method is switched by switching the format of components to reduce (compress) the data amount for an image signal that has little effect even when the image quality is reduced due to a reduction in data amount of the image signal by compression, and it is possible to reduce the compression of the band of the expansion bus (PCIe) 76.

Furthermore, in the above, an example of adjusting the compression rate by switching the bit packing method has been described. However, in a case of an image signal that is substantially a still image and does not require much frame rate, like a CT image, the data amount may be reduced by lowering the frame rate according to the type of image signal based on the information of DICOM IOD data.

By switching the frame rate according to the type of image signal in this way, it is possible to reduce the band of the expansion bus (PCIe) 76.

Moreover, regarding the bit packing method, it may be possible to uniformly switch to the same bit packing method within the frame, or, in a case where it is known that the image is an endoscopic image from a specific area in the frame, e.g., the DICOM IOD data, a bit packing method may be used that greatly reduces the image signal of the area outside the mask, which is almost black.

By switching the bit packing method for each area in the frame according to the type of the image signal in this way, it is possible to reduce the compression of the band of the expansion bus (PCIe) 76.

In either case, in the previous stage of the expansion bus (PCIe) 76, when the bit packing method for each area in the frame is switched or the frame rate is switched according to the type of the image signal, for image signals having little effect even when the data amount thereof is reduced, the data amount of the image signal is compressed to be reduced such that the compression of the band of the expansion bus (PCIe) 76 is suppressed.

Moreover, in the above, the bit packing units (BitPack) 73-1 to 73-n extract the type of the image signal on the basis of the ancillary data (DICOM IOD data) in the image signal of the decoded stream image and supply the type to the bit packing control unit (PackingCtrl) 74, but the type of image signal may be determined by a method other than DICOM IOD data.

That is, in a case where an image that does not include DICOM IOD data in the image signal is supplied, the bit packing unit (BitPack) 73 itself may analyze the image to determine the type of the image signal. For example, an image having a round black mask portion on the outer periphery may be determined to be an endoscopic image, and a grayscale image may be determined to be an X-ray image or a CT image. Furthermore, the type of the image may be determined according to an analysis result of a spatial frequency analysis or a dynamic range analysis of each channel of the Y, Cb, and Cr signals, and the bit packing method may be switched according to the determination result.

Furthermore, in the above, description is given of the example where information indicating what kind of bit packing method should be used is read from the table 75 and instructions are given to the bit packing unit 73 by the bit packing control unit (PackingCtrl) 74 of the IP converter reception apparatus 55 according to the type of the image signal recognized by the DICOM IOD data or the image analysis.

However, when it is possible to give instructions of the bit packing method, a configuration other than the bit packing control unit (PackingCtrl) 74 may give instructions. For example, the image management server 54 may give instructions as to which bit packing method to use according to the type of the image signal. More specifically, the image management server 54 may be able to rewrite the information of the bit packing method corresponding to the type of the image signal, which is registered in the table 75, and may function similarly to the bit packing control unit (PackingCtrl) 74 to directly give an instruction of the bit packing method to the bit packing unit 73.

4. Configuration Example of the Second Embodiment of the IP Converter Reception Apparatus In the above, description is given of the example where the bit packing method is switched according to the type of the image signal to reduce the data amount of image signal for an image signal that has little effect even when the data amount is reduced such that compression of the band of the expansion bus (PCIe) 76 is suppressed. However, the image signal may be encoded and decoded back by the GPU according to the type of the image signal.

Figure 5:
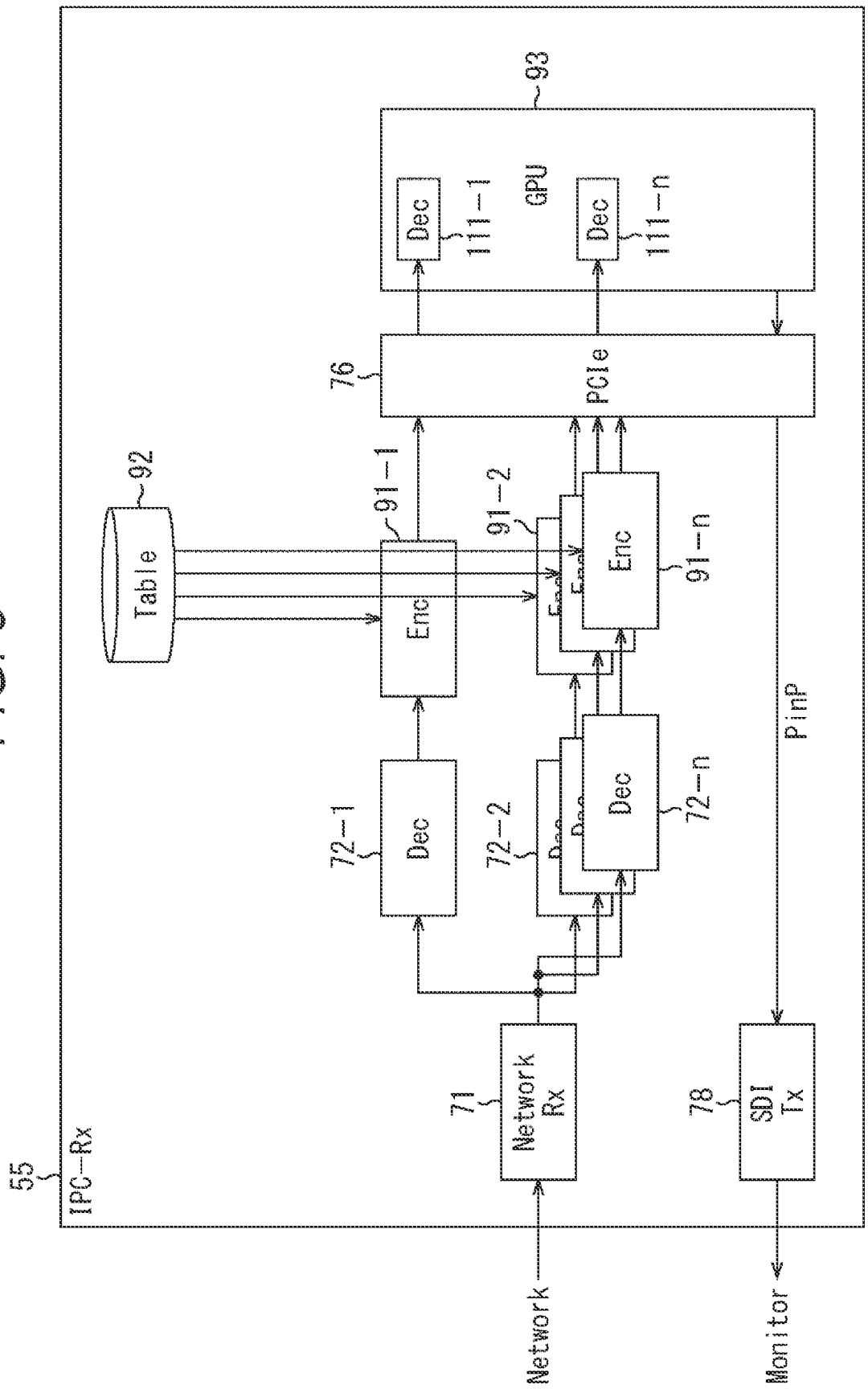
FIG. 5 is a diagram explaining a configuration example of a second embodiment of the IP converter reception apparatus.

FIG. 5 shows a configuration example of the second embodiment of the IP converter reception apparatus in which the image signal is encoded and decoded back by the GPU according to the type of the image signal to generate a single PinP image. Note that in the IP converter reception apparatus 55 of FIG. 5, the same reference numerals are given to the configurations having the same functions as the configuration of the IP converter reception apparatus 55 of FIG. 3, and the description thereof will be omitted as appropriate.

That is, the IP converter reception apparatus 55 of FIG. 5 differs from the IP converter reception apparatus 55 of FIG. 3 in that, instead of the bit packing units (BitPack) 73-1 to 73-n, the bit packing control unit (PackingCtrl) 74, the table (Table) 75, and the graphics processing unit (GPU) 77, encoders (Enc) 91-1 to 91-n, a table (Table) 92, and a graphics processing unit (GPU) 93 are provided.

The encoders (Enc) 91-1 to 91-n determine the type of the image signal decoded by the decoders (Dec) 72-1 to 72-n, read the information of a corresponding encoding method from the table 92 that stores the information of encoding methods according to the type of the image signal, encodes the image signal by the read encoding method, and outputs the image signal to the GPU 93 via the expansion bus (PCIe) 76. The encoding method used in the encoder 91 is, for example, lossless compression JPEG2000, lossless compression DPCM, or the like.

The graphics processing unit (GPU) 93 includes decoders (Dec) 111-1 to 111-n that decode the encoded image signal corresponding to each of the encoders (Enc) 91-1 to 91-n, generate a single picture in picture (PinP) image by image processing that combines a plurality of decoded images, and outputs the image to the expansion bus 76.

That is, with the above configuration, for example, an encoding method is selected according to the type of the supplied image signal, and for image signals having little effect even when the data amount thereof is reduced, an encoding method that increases the compression rate is selected. Therefore, it is possible to reduce the compression of the band of the expansion bus (PCIe) 76 by reducing the data amount and compressing the types of images that have no effect even when the image quality is reduced.

As a result, it is possible to suppress a reduction in resolution of an image that a surgery operator wants to see at a high resolution while responding to an increase in the number of connections of medical equipment that supply images.

<Display Control Processing by the IP Converter Reception Apparatus of FIG. 5>

Figure 6:
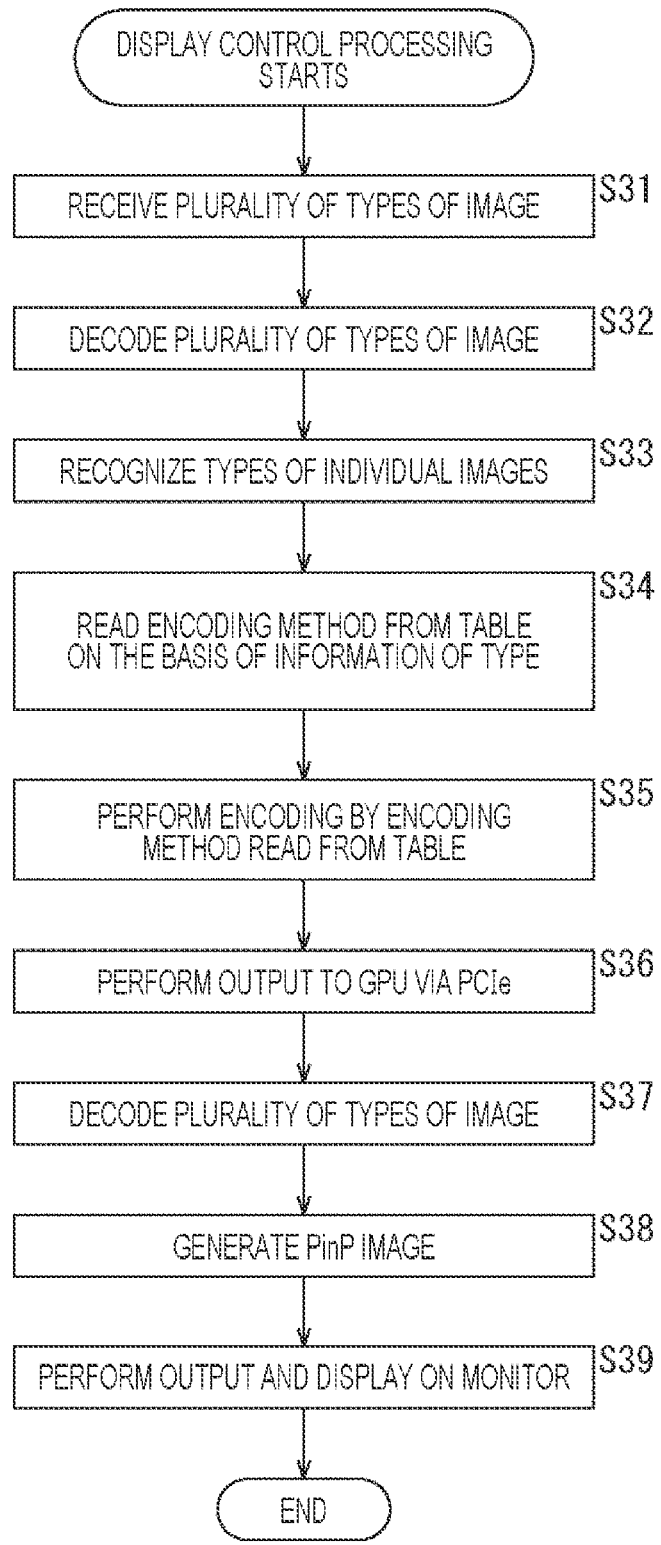
FIG. 6 is a flowchart explaining display control processing by the IP converter reception apparatus of FIG. 5.

Next, the display control processing by an IP converter reception apparatus of FIG. 5 will be described with reference to the flowchart of FIG. 6.

In step S31, the input unit (Network Rx) 71 accepts an input of a plurality of types of stream images and outputs them to the decoders 72-1 to 72-n that decode the corresponding stream images according to the type of encoding.

In step S32, the decoders (Decoder) 72-1 to 72-n decode the encoded stream images for each encoding type and output the decoded stream images to the respective encoders (Enc) 91-1 to 91-n.

In step S33, the encoders (Enc) 91-1 to 91-n extract and recognize the information of the type of individual image signal on the basis of the ancillary data (DICOM data) in the image signal of the decoded stream image.

In step S34, the encoders (Enc) 91-1 to 91-n access the table (Table) 92 and read information of an encoding method according to the type of recognized image signal.

In step S35, the encoders (Enc) 91-1 to 91-n encode the image signal by the read encoding method.

In step S36, the encoders (Enc) 91-1 to 91-n output the encoded image signal to the GPU 93 via the expansion bus (PCIe) 76.

In step S37, the graphics processing unit (GPU) 93 controls each of the decoders (Dec) 111-1 to 111-n to decode the image signal encoded by a method corresponding to each of the encoders (Enc) 91-1 to 91-n.

In step S38, the GPU 93 generates a single picture in picture (PinP) image by image processing that combines a plurality of decoded images, and outputs the image to the output unit 78 via the expansion bus 76.

In step S39, the output unit (serial digital interface (SDI)) 78 outputs the image signal of the PinP image to the monitor 56 provided in the surgery room and including the display and causes the monitor to display the image.

By the above processing, in the previous stage of the expansion bus (PCIe) 76, the encoding method is switched according to the type of the image signal. For the image signal that has little effect even when the image quality is reduced due to a reduction in data amount by encoding of the image signal, encoding is performed so that the data amount is reduced (compressed), such that the compression of the band of the expansion bus (PCIe) 76 can be suppressed.

As a result, it is possible to suppress a reduction in resolution of an image that a surgery operator wants to see at a high resolution while responding to an increase in the number of connections of medical equipment that supply images.

Furthermore, in the above, description is given of the example in which the information indicating what kind of encoding method should be used according to the type of the image signal recognized by the DICOM IOD data or image analysis is read from the table 92 by the encoder (Enc) 91 of the IP converter reception apparatus 55, and the encoder 91 makes determination. However, as long as the encoding method can be determined, it may be determined by other than the encoder 91. For example, the image management server 54 may give an instruction to the encoder 91 as to which encoding method to use according to the type of the image signal.

5. Configuration Example of the Third Embodiment of the IP Converter Reception Apparatus In the above, description is given of the example in which the bit packing method or encoding method is switched according to the type of the image signal to compress and reduce the data amount for the image signal that has little effect even when the data amount of the image signal is reduced such that compression of the band of the expansion bus (PCIe) 76 is suppressed. However, the bit packing format may be switched according to the processing load on the GPU.

The GPU is subjected to varying processing loads depending on the format of data in the image signal processing. That is, in a case of a format including 16-bit alignment, the GPU does not require extra computing resources for reading the data, so that the processing load is reduced. Therefore, even for an image signal that is reduced in base image quality, it is possible to perform advanced processing for recognition processing or the like.

On the other hand, in a case where band compression is prioritized and the format is not 16-bit alignment, the GPU will use computing resources to read it, resulting in a reduction in image processing that can be performed.

Therefore, the bit packing format may be switched according to the load status of the GPU.

Figure 7:
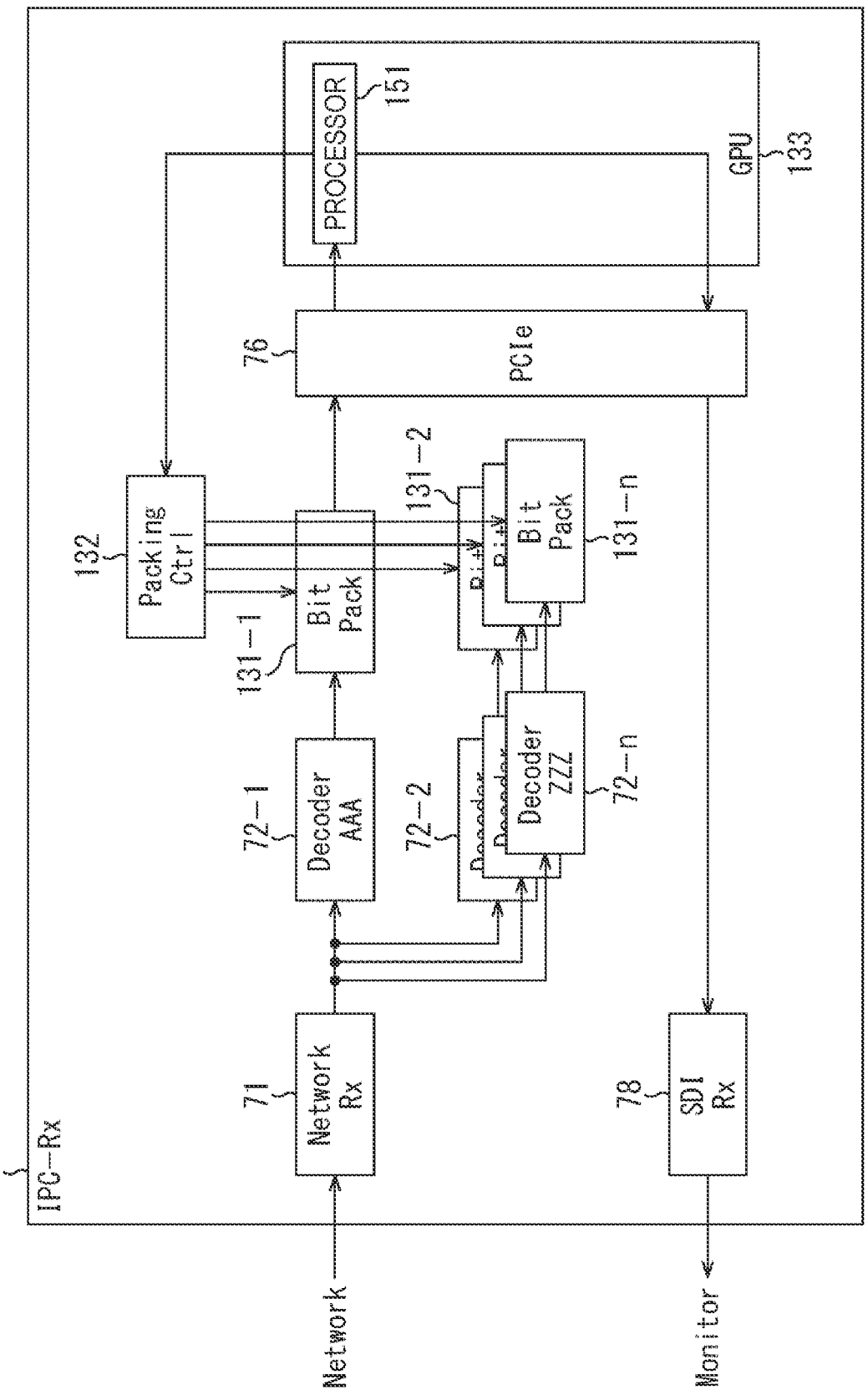
FIG. 7 is a diagram explaining a configuration example of a third embodiment of the IP converter reception apparatus.

FIG. 7 shows a configuration example of the third embodiment of the IP converter reception apparatus in which the bit packing format is switched according to the load status of the GPU. Note that in the IP converter reception apparatus 55 of FIG. 7, the same reference numerals are given to the configurations having the same functions as the configuration of the IP converter reception apparatus 55 of FIG. 3, and the description thereof will be omitted as appropriate.

That is, the IP converter reception apparatus 55 of FIG. 7 differs from the IP converter reception apparatus 55 of FIG. 3 in that, instead of the bit packing units (BitPack) 73-1 to 73-n, the bit packing control unit (PackingCtrl) 74, the table (Table) 75, and the graphics processing unit (GPU) 77, bit packing units (BitPack) 131-1 to 131-n, a bit packing control unit (PackingCtrl) 132, and a graphics processing unit (GPU) 133 are provided.

The bit packing units (BitPack) 131-1 to 131-n bit-pack the decoded image signal according to the type of the image signal in a format according to the processing load of the GPU 133 supplied from the bit packing control unit 132, and output the image signal to the GPU 133 via the expansion bus (PCIe) 76.

The GPU 133 includes a processor 151, and information of the processing load of the processor 151 is read by the bit packing control unit 132.

The bit packing control unit 132 outputs information of the bit packing format according to the processing load of the processor 151 of the GPU 133 to the bit packing units (BitPack) 131-1 to 131-n.

<Bit Packing Format>

Here, with reference to FIG. 8, the bit packing format according to the processing load of the processor 151 of the GPU 133 will be described.

Figure 8:
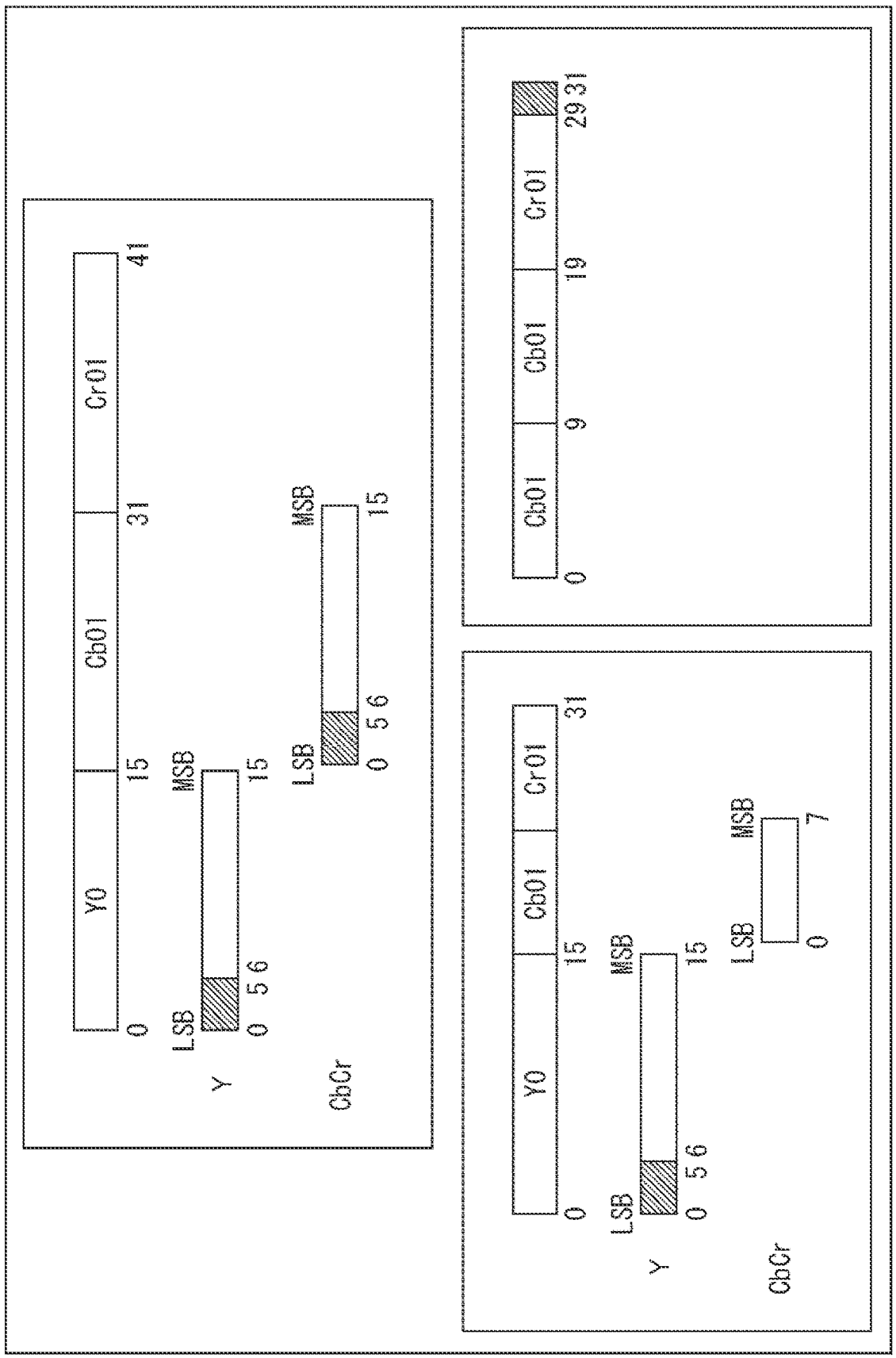
FIG. 8 is a diagram explaining a bit packing format.

Normally, as shown in the upper part of FIG. 8, a Y signal and Cb and Cr signals represented by Y0, Cb01, and Cr01 are each bit-packed in a 16-bit aligned 16-bit packing format formed every 16 bits.

Note that, in the upper part of FIG. 8, each of the Y signal and the Cb and Cr signals has 6 bits as the remainder bits from the LSB and the remaining 10 bits as the payload.

That is, since each signal is 16-bit aligned, the processor 151 of the GPU 133 that handles floating point numbers reads data in 16-bit units, and because of good data access, data can be read with a low load.

Here, in the case of the 16-bit packing format, since each of the Y, Cb, and Cr signals is 16 bits, the total data amount is 48 bits. Note that, in the upper part of FIG. 8, YCbCr is a component format 422, and each signal is data including 10 bits.

For this reason, when all of the images are in the 48-bit data format, the band of the expansion bus (PCIe) 76 will be compressed as the number of image types increases.

Therefore, two types of bit packing formats shown in the lower part of FIG. 8 can be considered.

The first bit packing format is a hetero-packing format in which, as shown in the lower left part of FIG. 8, a Y signal represented by Y0 is 16 bits, and Cb and Cr signals represented by Cb01 and Cr01 are each 8 bits.

In the hetero-packing format in the lower left part of FIG. 8, 6 bits from the LSB of the Y signal represented by Y0 are the remainder bits, the remaining 10 bits are the payload, and Cb and Cr signals represented by Cb01 and Cr01 each have 8 bits as the payload.

In the case of the hetero-packing format in the lower left part of FIG. 8, the Y signal is 16 bits without reductions in data amount, and the Cb signal and Cr signal are each 8 bits to have a total of 16 bits. Therefore, the base image quality is reduced by the reduction in data amount of the Cb and Cr signals, but because the processing load of the processor 151 on the GPU 133 is low, it is possible to perform advanced processing for recognition processing or the like.

On the other hand, the second bit packing format is a high compression packing format in which, as shown in the lower right part of FIG. 8, each of the Y signal and the Cb and Cr signals is 10 bits.

In the high compression packing format in the lower right part of FIG. 8, each of the Y signal and the Cb and Cr signals represented by Y0, Cb01, and Cr01 has 10 bits from the LSB as the payload, and the remaining 2 bits is the remainder bits.

In the case of the high compression packing format in the lower right part of FIG. 8, the Y, Cb, and Cr signals are all 10 bits. A reduction in data amount of the Y, Cb, and Cr signals is small as compared to the hetero-packing format, and thus compression has been performed at high efficiency, accordingly, and a reduction in base image quality can be suppressed as compared with the hetero-packing format. However, since the format in the lower right part of FIG. 8 is data that is not in 16-bit units, the processing load of the processor 151 on the GPU 133 related to reading becomes high, so that a lot of resources are required to read the data and other advanced processing cannot be performed, accordingly.

Therefore, in a case where the processing load of the processor 151 of the GPU 133 is lower than a predetermined threshold value, control is performed such that bit punking is performed by the high compression packing format shown in the middle of FIG. 9 with respect to the 16-bit packing format in which the compression of the band of the normal expansion bus (PCIe) 76 shown in the upper part of FIG. 9 is large (indicated as "NG" in the drawing). The high compression packing format can reduce the compression of the band on the expansion bus (PCIe) 76 (indicated as "OK" in the drawing), but the processing load of the processor 151 on the GPU 133 becomes high load (unpack is high load), so that advanced signal processing by the GPU 133 becomes impossible (GPU signal processing becomes poor).

On the other hand, in a case where the processing load of the processor 151 of the GPU 133 is higher than a predetermined threshold value, control is performed such that bit punking is performed by the hetero-packing format shown in the middle of FIG. 9. The hetero-packing format can reduce the compression of the band on the expansion bus (PCIe) 76 (indicated as "OK" in the drawing) and enables reading of data in 16-bit units. Therefore, the processing load of the processor 151 on the GPU 133 becomes low load (unpack is low load), so that advanced signal processing becomes possible (GPU signal processing becomes rich).

<Display Control Processing by the IP Converter Reception Apparatus of FIG. 7>

Figure 10:
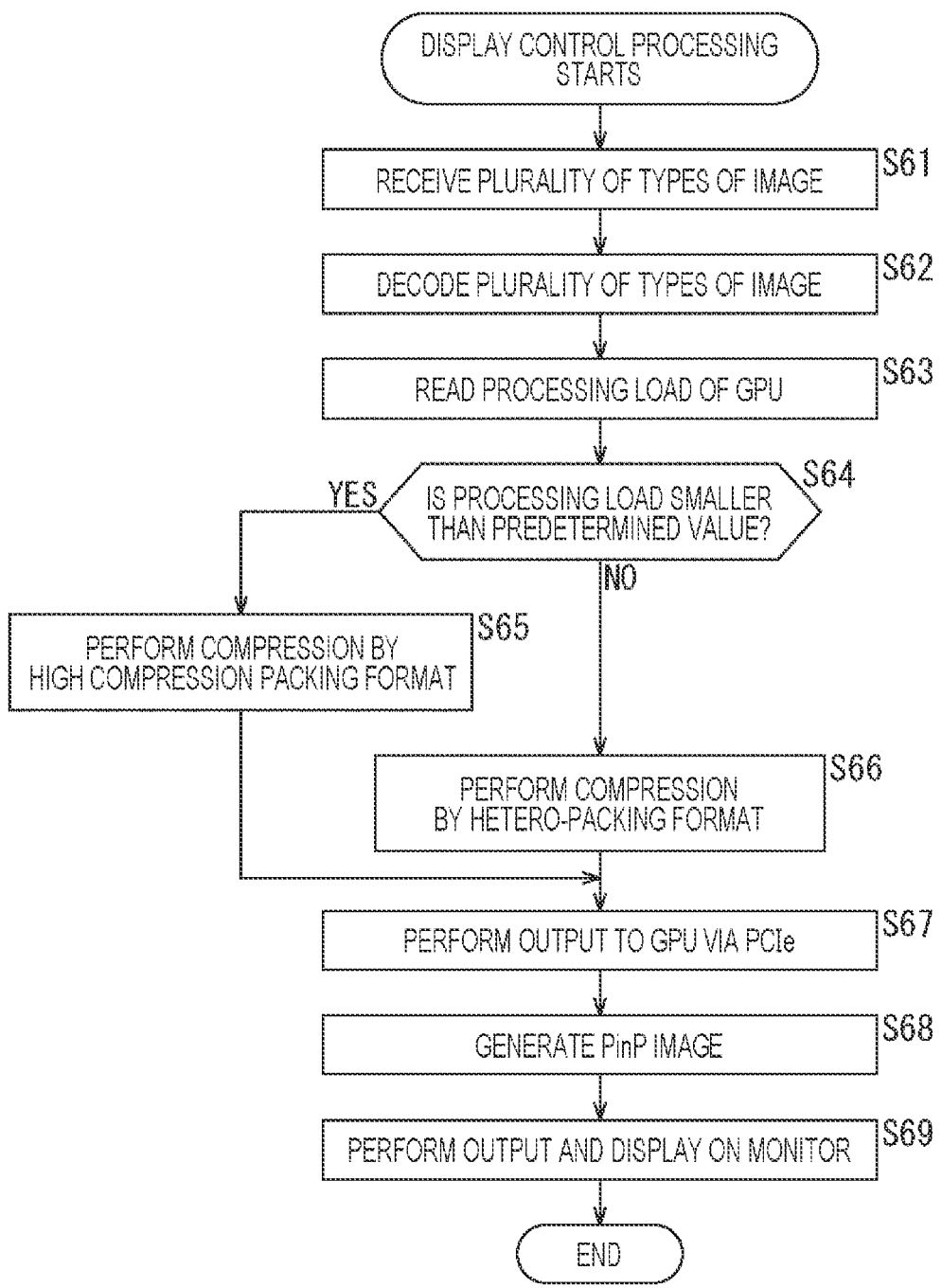
FIG. 10 is a flowchart explaining display control processing by the IP converter reception apparatus of FIG. 7.

Next, the display control processing by an IP converter reception apparatus 55 of FIG. 7 will be described with reference to the flowchart of FIG. 10.

In step S61, the input unit (Network Rx) 71 accepts an input of a plurality of types of stream images and outputs them to the decoders 72-1 to 72-n that decode the corresponding stream images according to the type of encoding.

In step S62, the decoders (Decoder) 72-1 to 72-n decode the types of stream images for each type of encoding, and output the decoded stream images to the respective bit packing units 131-1 to 131-n.

In step S63, the bit packing control unit (PackingCtrl) 132 reads the load of the processor 151 of the GPU 133.

In step S64, the bit packing control unit (PackingCtrl) 132 determines whether or not the processing load of the processor 151 of the GPU 133 is lower than the predetermined value (threshold value), and in a case where it is lower than the predetermined value, the processing proceeds to step S66.

In step S65, the bit packing control unit (PackingCtrl) 132 gives an instruction to the bit packing units (BitPack) 131-1 to 131-n to perform bit packing by the high compression packing format described with reference to the lower right part of FIG. 8.

On the basis of this instruction, the bit packing units (BitPack) 131-1 to 131-n bit-pack the image signal by the high compression packing format.

On the other hand, in step S64, in a case where the processing load of the processor 151 of the GPU 133 is not lower than the predetermined threshold value, the processing proceeds to step S66.

In step S66, the bit packing control unit (PackingCtrl) 132 gives an instruction to the bit packing units (BitPack) 131-1 to 131-n to perform bit packing by the hetero-packing format described with reference to the lower left part of FIG. 8.

On the basis of this instruction, the bit packing units (BitPack) 131-1 to 131-n bit-pack the image signal by the hetero-packing format.

In step S67, the bit packing units (BitPack) 131-1 to 131-n output the bit-packed image signal to the GPU 133 via the expansion bus (PCIe) 76.

In step S68, the graphics processing unit (GPU) 133 generates a single picture in picture (PinP) image by image processing that uses a plurality of images, and outputs the image to the output unit 78 via the expansion bus 76.

In step S69, the output unit (serial digital interface (SDI)) 78 outputs the image signal of the PinP image to the monitor 56 provided in the surgery room and including the display and causes the monitor to display the image.

Note that, needless to say, in both of the processing of steps S65 and S66, the bit packing units (BitPack) 131-1 to 131-n may switch the bit packing format according to the processing load of the processor 151 of the GPU 133 and may switch the bit packing method according to the type of the image.

By the above processing, in the previous stage of the expansion bus (PCIe) 76, the bit packing format is switched according to the processing load of the GPU, so that for the image signal that has little effect even when the data amount of the image signal is reduced, the data amount is reduced, and it becomes possible to suppress the compression of the band of the expansion bus (PCIe) 76.

Furthermore, when the processing load of the GPU 133 is low and a sufficient processing capacity can be secured, it is possible to suppress a reduction in image quality due to data by the high compression bit packing format while suppressing band compression.

Moreover, when the processing load of the GPU 133 is high and a sufficient processing capacity cannot be secured, the hetero-bit packing format allows a reduction in image quality due to data, but it is possible to suppress an increase in processing load due to the GPU 133.

As a result, it is possible to suppress a reduction in resolution of an image that a surgery operator wants to see at a high resolution while responding to an increase in the number of connections of medical equipment that supply images.

Note that, in the above, the configuration in which the processor 151 in the GPS 133 controls the bit packing control unit (PackingCtrl) 132 has been described, but a separate processor such as a CPU may be present in the IPC-Rx 55 and the processor may read the register of the GPU 133 to control the bit packing control unit (PackingCtrl) 132 on the basis of the result.

Furthermore, in the above, an example in which the expansion bus 76, which is a data transmission path, is PCIe has been described, but as long as it functions as a data transmission path, it can be applied to other configurations. For example, it may be applied to mobile industry processor interface (MIPI), gigabit multimedia serial link (GMSL), or the like, which functions as a data transmission path.

Moreover, in the above, an example in which a single PinP image is generated by image processing that combines a plurality of types of image signals and presented to the surgery operator has been described, but even in the case of a 3D image that presents at least two images for the left and right eyes, the compression of the band of the expansion bus (PCIe) 76 can be suppressed by similar handling.

With such a configuration, for example, whether or not the monitor 56 supports 3D display cannot be recognized by the camera 50 or the image management server 54 in the hospital. Therefore, image signals for both the left and right eyes are transmitted to the IP converter reception apparatus (IPC-Rx) 55.

The IP converter reception apparatus (IPC-Rx) 55 may perform control to switch the image signals for both the left and right eyes in the previous stage of the expansion bus (PCIe) 76 according to the display function of the monitor 56 to which the IP converter reception apparatus is connected, to, for example, a Line by Line image (progressive image signal), a Top and Bottom image signal (interlaced image signal), or a 2D image signal, and output the image signal to the GPU 77.

6. Example of Execution by Software

Incidentally, the series of processing described above can be executed by hardware, but it can also be executed by software. In a case where the series of processing is executed by software, a program that constitutes the software is installed, from a recording medium, in a computer incorporated in a dedicated hardware or, for example, in a general-purpose computer and the like that can execute various functions when various programs are installed.

Figure 11:
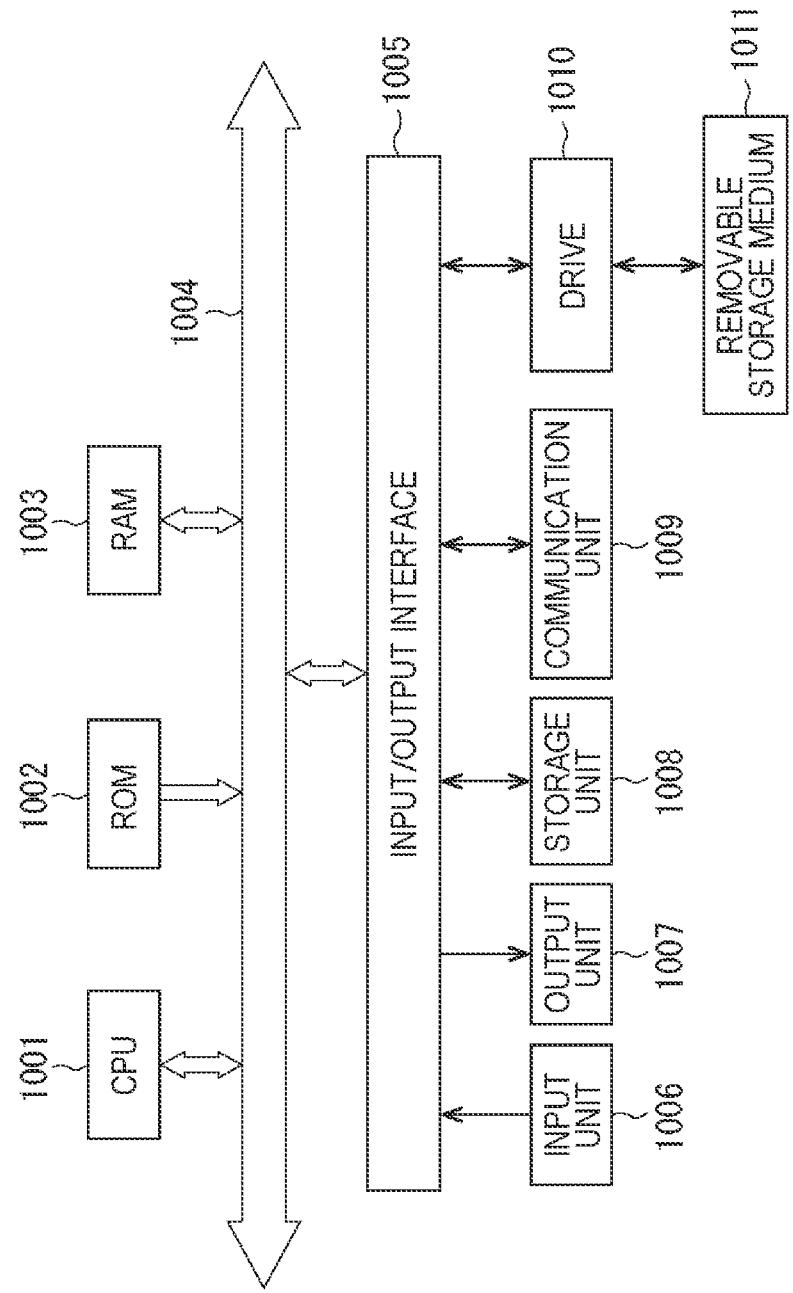
FIG. 11 is a diagram explaining a configuration example of a general-purpose personal computer.

FIG. 11 shows a configuration example of a general-purpose computer. This personal computer incorporates a central processing unit (CPU) 1001. An input/output interface 1005 is connected to the CPU 1001 via a bus 1004. A read only memory (ROM) 1002 and a random access memory (RAM) 1003 are connected to the bus 1004.

An input unit 1006 including an input device including a keyboard, a mouse, or the like with which the user inputs an operation command, an output unit 1007 that outputs a processing manipulation screen or an image of processing results to a display device, a storage unit 1008 including a hard disk drive or the like storing a program or various data, and a communication unit 1009 including a local area network (LAN) adapter or the like and executing communication processing via a network represented by the Internet are connected to the input/output interface 1005. Furthermore, a drive 1010 that reads and writes data with respect to a removable storage medium 1011, e.g., a magnetic disk (including a flexible disk), an optical disk (including a compact disc-read only memory (CD-ROM), a digital versatile disc (DVD)), a magneto-optical disk (including mini disc (MD)), or a semiconductor memory is connected.

The CPU 1001 executes various processing according to a program stored in the ROM 1002 or a program that is read from the removable storage medium 1011, e.g., a magnetic disk, an optical disk, a magneto-optical disk, or a semiconductor memory, installed in the storage unit 1008, and loaded on the RAM 1003 from the storage unit 1008. Data or the like required for the CPU 1001 to execute various processing are also stored in the RAM 1003 as appropriate.

In a computer configured in the aforementioned manner, for example, the CPU 1001 loads a program stored in the storage unit 1008 on the RAM 1003 via the input/output interface 1005 and the bus 1004 and executes the program, and thus the aforementioned series of processing is carried out.

The program to be executed by the computer (CPU 1001) can be provided by being recorded on the removable storage medium 1011, for example, as a package medium or the like. Furthermore, the program can be provided via a wired or wireless transmission medium such as a local area network, the Internet, or digital satellite broadcasting.

In the computer, the program can be installed in the storage unit 1008 via the input/output interface 1005 when the removable storage medium 1011 is mounted on the drive 1010. Furthermore, the program can be received by the communication unit 1009 via a wired or wireless transmission medium and installed in the storage unit 1008. In addition, the program can be pre-installed in the ROM 1002 or the storage unit 1008.

Note that the program executed by the computer may be a program that is processed in chronological order along the order described in the present description or may be a program that is processed in parallel or at a required timing, e.g., when call is carried out.

Note that the CPU 1001 in FIG. 11 realizes functions of the decoders 72-1 to 72-$n$, the bit packing units 73-1 to 73-$n$, the bit packing control unit 74 of FIG. 3, the encoders 91-1 to 91-$n$ of FIG. 5, or the decoders 72-1 to 72-$n$, the bit packing units 131-1 to 131-$n$, and the bit packing control unit 132 of FIG. 7.

Furthermore, in the present description, the system means a cluster of a plurality of constituent elements (an apparatus, a module (component), or the like), and it does not matter whether or not all the constituent elements are present in the same enclosure. Therefore, a plurality of apparatuses that is housed in different enclosures and connected via a network, and a single apparatus in which a plurality of modules is housed in a single enclosure are both the system.

Note that an embodiment of the present disclosure is not limited to the aforementioned embodiments, and various changes may be made within a scope without departing from the gist of the present disclosure.

For example, the present disclosure can adopt a configuration of cloud computing in which one function is shared and jointly processed by a plurality of apparatuses via a network.

Furthermore, each step described in the above-described flowcharts can be executed by a single apparatus or shared and executed by a plurality of apparatuses.

Moreover, in a case where a single step includes a plurality of pieces of processing, the plurality of pieces of processing included in the single step can be executed by a single apparatus or can be shared and executed by a plurality of apparatuses.

7. Application Example

The technology according to the present disclosure is applicable to a variety of products. For example, the technology according to the present disclosure may be applied to a surgery room system.

Figure 12:
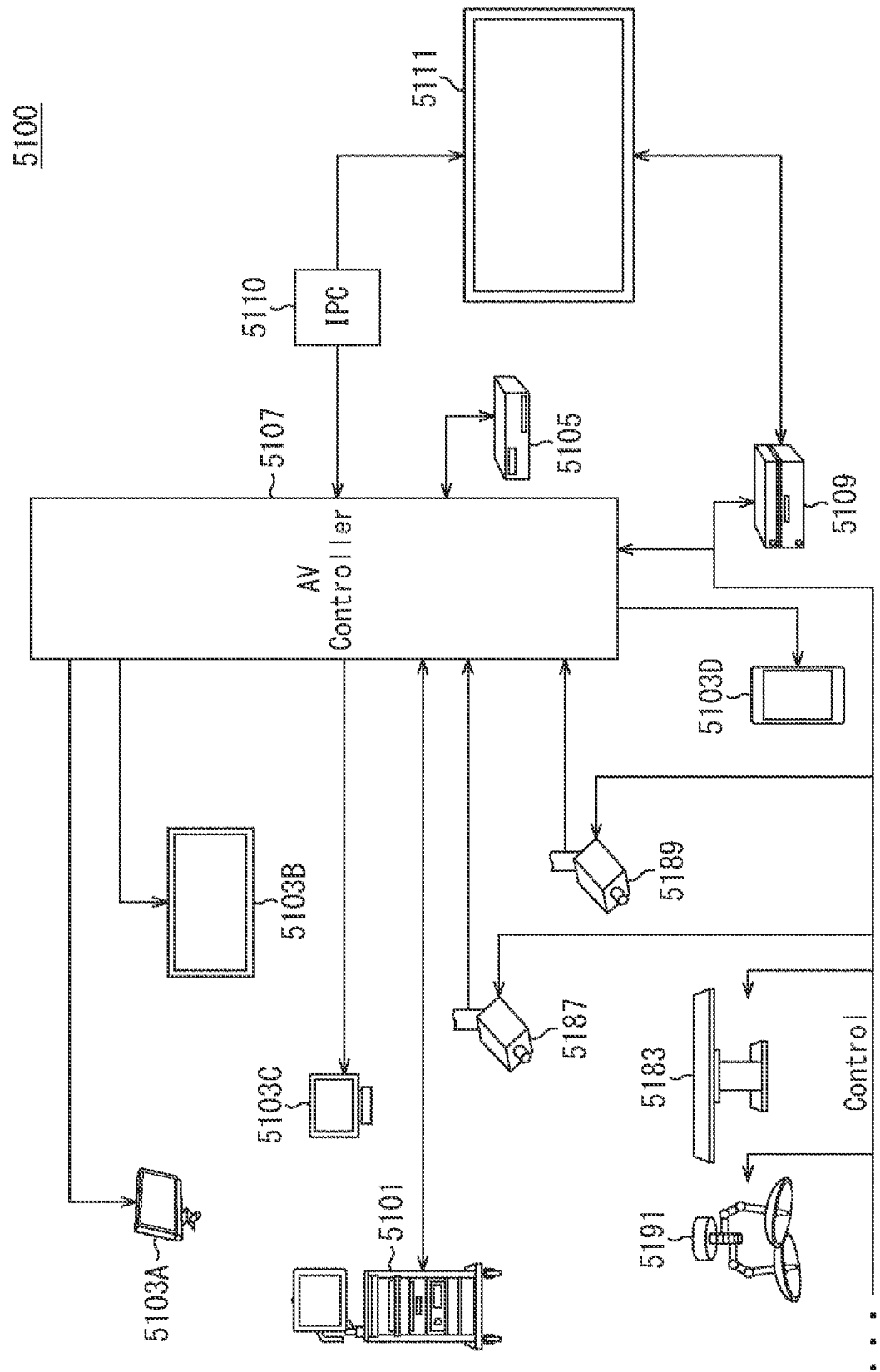
FIG. 12 is a diagram schematically showing the overall configuration of a surgery room system.

FIG. 12 is a diagram schematically showing the overall configuration of a surgery room system 5100 to which the technology according to the present disclosure can be applied. With reference to FIG. 12, the surgery room system 5100 is configured such that an apparatus group installed in a surgery room is connected to be capable of cooperating with each other through an audiovisual controller (AV controller) 5107 and a surgery room control apparatus 5109.

In the surgery room, various apparatuses can be provided. In FIG. 12, as an example, various apparatus groups 5101 for an endoscopic surgery, a ceiling camera 5187 which is disposed on the ceiling of the surgery room, and images the hands of a surgery operator, a surgery site camera 5189 which is disposed on the ceiling of the surgery room, and images the entire state of the surgery room, a plurality of display apparatuses 5103A to 5103D, a recorder 5105, a patient bed 5183, and an illumination 5191, are shown.

Here, among these apparatuses, the apparatus group 5101 belongs to an endoscope surgery system 5113 as described later, and includes an endoscope, a display apparatus displaying an image imaged by the endoscope, and the like. Each of the apparatuses belonging to the endoscope surgery system 5113 is also referred to as medical equipment. On the other hand, the display apparatuses 5103A to 5103D, the recorder 5105, the patient bed 5183, and the illumination 5191, for example, are apparatuses provided in the surgery room, separately from the endoscope surgery system 5113. Each of the apparatuses not belonging to the endoscope surgery system 5113, is also referred to as non-medical equipment. The audiovisual controller 5107 and/or the surgery room control apparatus 5109 cooperatively control the operation of the medical equipment and the non-medical equipment.

The audiovisual controller 5107 integrally controls processing relevant to image display in the medical equipment and the non-medical equipment. Specifically, in the apparatuses of the surgery room system 5100, the apparatus group 5101, the ceiling camera 5187, and the surgery site camera 5189 can be an apparatus having a function of transmitting information to be displayed during the surgery (hereinafter, also referred to as display information) (hereinafter, also referred to as an apparatus of a transmission source). Furthermore, the display apparatuses 5103A to 5103D can be an apparatus to which the display information is output (hereinafter, also referred to as an apparatus of an output destination). Furthermore, the recorder 5105 can be an apparatus corresponding to both of the apparatus of the transmission source and the apparatus of the output destination. The audiovisual controller 5107 has a function of controlling the operation of the apparatus of the transmission source and the apparatus of the output destination, of acquiring the display information from the apparatus of the transmission source, of transmitting the display information to the apparatus of the output destination, and of causing the display information to be displayed or recorded. Note that the display information is various images imaged during the surgery, various information associated with the surgery (for example, body information of a patient, a test result of the past, information associated with a surgery method, or the like), and the like.

Specifically, information with respect to an image of a surgery portion in body cavity of the patient, which is imaged by the endoscope, can be transmitted to the audiovisual controller 5107 from the apparatus group 5101, as the display information. Furthermore, information with respect to an image of the hands of the surgery operator, which is imaged by the ceiling camera 5187, can be transmitted from the ceiling camera 5187, as the display information. Furthermore, information with respect to an image indicating the entire state of the surgery room, which is imaged by the surgery site camera 5189, can be transmitted from the surgery site camera 5189, as the display information. Note that in a case where the other apparatus having an imaging function exists in the surgery room system 5100, the audiovisual controller 5107 may acquire information with respect to an image imaged by the other apparatus from the other apparatus, as the display information.

Alternatively, for example, in the recorder 5105, the information with respect to the image imaged in the past is recorded by the audiovisual controller 5107. The audiovisual controller 5107 is capable of acquiring the information with respect to the image imaged in the past, from the recorder 5105, as the display information. Note that, in the recorder 5105, various information associated with the surgery may be also recorded in advance.

The audiovisual controller 5107 displays the acquired display information (i.e., an image captured during the surgery or various information associated with the surgery) on at least one of the display apparatuses 5103A to 5103D, which are the apparatus of the output destination. In the shown example, the display apparatus 5103A is a display apparatus disposed to be suspended from the ceiling of the surgery room, the display apparatus 5103B is a display apparatus disposed on a wall surface of the surgery room, the display apparatus 5103C is a display apparatus disposed on a desk in the surgery room, and the display apparatus 5103D is mobile equipment having a display function (for example, a tablet personal computer (PC)).

Furthermore, even though it is not shown in FIG. 12, the surgery room system 5100 may include an apparatus outside the surgery room. The apparatus outside the surgery room, for example, can be a server connected to a network constructed inside or outside the hospital, or a PC used by a medical staff, a projector disposed in an assembly room of the hospital, and the like. In a case where such an external apparatus is outside the hospital, the audiovisual controller 5107 is capable of displaying the display information on a display apparatus of the other hospital through a teleconference system or the like, in order for a remote medical care.

The surgery room control apparatus 5109 integrally controls processing other than the processing relevant to the image display in the non-medical equipment. For example, the surgery room control apparatus 5109 controls the driving of the patient bed 5183, the ceiling camera 5187, the surgery site camera 5189, and the illumination 5191.

An IP converter apparatus (IPC) 5110 is an apparatus that accepts input of a plurality of IP-packetized images corresponding to the display information transmitted from the transmission source apparatus and output from the audiovisual controller 5107, performs decoding for each image type, and converts the image into an image signal. At this time, a plurality of images may be combined to generate a single PinP image. The IP converter apparatus 5110 outputs an image signal to a centralized manipulation panel 5111 and causes the centralized manipulation panel 5111 to display it.

Note that the IP converter apparatus 5110 may have a function of converting an image signal output from a display device into an IP packet.

In the surgery room system 5100, a centralized manipulation panel 5111 is provided. A user is capable of giving an instruction with respect to the image display, to the audiovisual controller 5107, or of giving an instruction regarding the operation of the non-medical equipment, to the surgery room control apparatus 5109, through the centralized manipulation panel 5111. The centralized manipulation panel 5111 has a configuration in which a touch panel is disposed on a display surface of the display apparatus.

Figure 13:
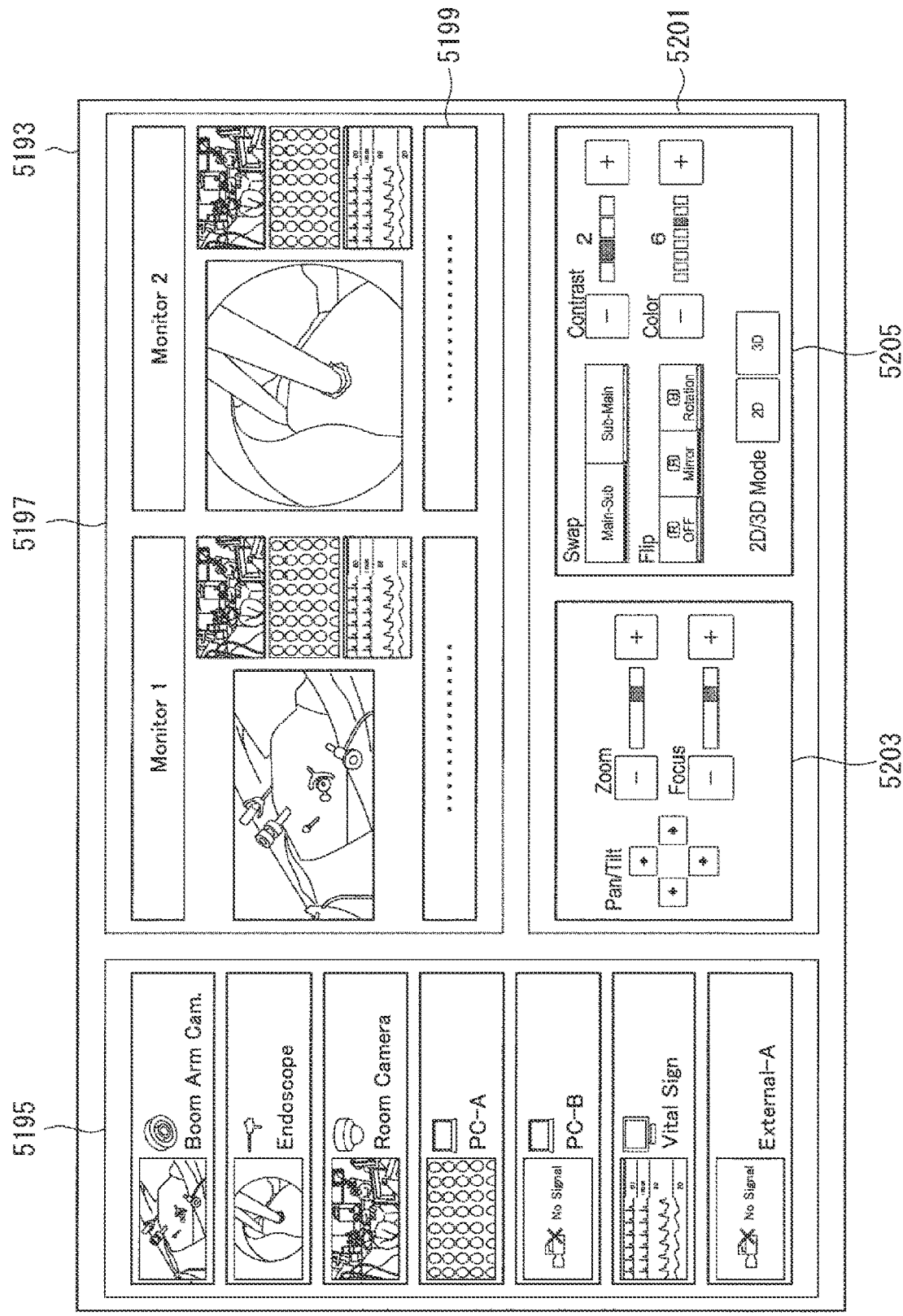
FIG. 13 is a diagram showing a display example of a manipulation screen on a centralized manipulation panel.

FIG. 13 is a diagram showing a display example of a manipulation screen of the centralized manipulation panel 5111. In FIG. 13, as an example, a manipulation screen corresponding to a case where two display apparatuses are provided in the surgery room system 5100, as the apparatus of the output destination, is shown. With reference to FIG. 13, in the manipulation screen 5193, a transmission source selection region 5195, a preview region 5197, and a control region 5201 are provided.

On the transmission source selection region 5195, a transmission source apparatus provided in the surgery room system 5100, and a thumbnail screen indicating display information of the transmission source apparatus, are displayed to be linked to each other. The user is capable of selecting the display information that he/she wants to display on the display apparatus, from any transmission source apparatus displayed on the transmission source selection region 5195.

On the preview region 5197, a preview of a screen to be displayed on two display apparatuses (Monitor 1 and Monitor 2), which are the apparatus of the output destination, is displayed. In the shown example, four images are PinP-displayed on one display apparatus. The four images correspond to the display information transmitted from the transmission source apparatus selected in the transmission source selection region 5195. Among the four images, one image is displayed comparatively large as a main image, and the remaining three images are displayed comparatively small as a sub-image. The user suitably selects an area on which four images are displayed, and thus is capable of switching between the main image and the sub-image. Furthermore, in a lower portion of the area on which four images are displayed, a status display region 5199 is provided. A status relevant to the surgery (for example, an elapsed time of the surgery, the body information of the patient, and the like) can be suitably displayed on the area.

In the control region 5201, a transmission source manipulation region 5203 on which a graphical user interface (GUI) component for performing a manipulation with respect to the apparatus of the transmission source, is displayed, and an output destination manipulation region 5205 on which a GUI component for performing a manipulation with respect to the apparatus of the output destination, is displayed, are provided. In the shown example, in the transmission source manipulation region 5203, a GUI component for performing various manipulations (pan, tilt, and zoom) with respect to a camera in the apparatus of the transmission source having an imaging function, is provided. The user suitably selects the GUI component, and thus, is capable of manipulating the operation of the camera in the apparatus of the transmission source. Note that, even though it is not shown in the drawing, in a case where the apparatus of the transmission source selected in the transmission source selection region 5195 is a recorder (i.e., in a case where the image recorded in the recorder in the past is displayed on the preview region 5197), in the transmission source manipulation region 5203, a GUI component for performing a manipulation such as reproducing, stopping reproducing, rewinding, and fast forwarding of the image, can be provided.

Furthermore, in the output destination manipulation region 5205, a GUI component for performing various manipulations (swap, flip, tone adjustment, contrast adjustment, and switching between 2D display and 3D display) with respect to the display on the display apparatus, which is the apparatus of the output destination, is provided. The user suitably selects such a GUI component, and thus, is capable of manipulating the display on the display apparatus.

Note that the manipulation screen to be displayed on the centralized manipulation panel 5111 is not limited to the shown example, and the user may perform manipulation input with respect to each apparatus, which is provided in the surgery room system 5100, and is capable of being controlled by the audiovisual controller 5107 and the surgery room control apparatus 5109, through the centralized manipulation panel 5111.

FIG. 13 is a diagram showing an example of the state of the surgery to which the surgery room system described above is applied. The ceiling camera 5187 and the surgery site camera 5189 are disposed on the ceiling of the surgery room, and are capable of capturing the hands of a surgery operator (a surgeon) 5181 performing a treatment with respect to an affected part of a patient 5185 on the patient bed 5183, and the entire state of the surgery room. In the ceiling camera 5187 and the surgery site camera 5189, a magnification adjustment function, a focal point distance adjustment function, a capturing direction adjustment function, and the like can be provided. The illumination 5191 is disposed on the ceiling of the surgery room, and irradiates at least the hands of the surgery operator 5181 with light. The illumination 5191 may suitably adjust an irradiation light amount, a wavelength (a color) of irradiation light, a light irradiation direction, and the like.

Figure 14:
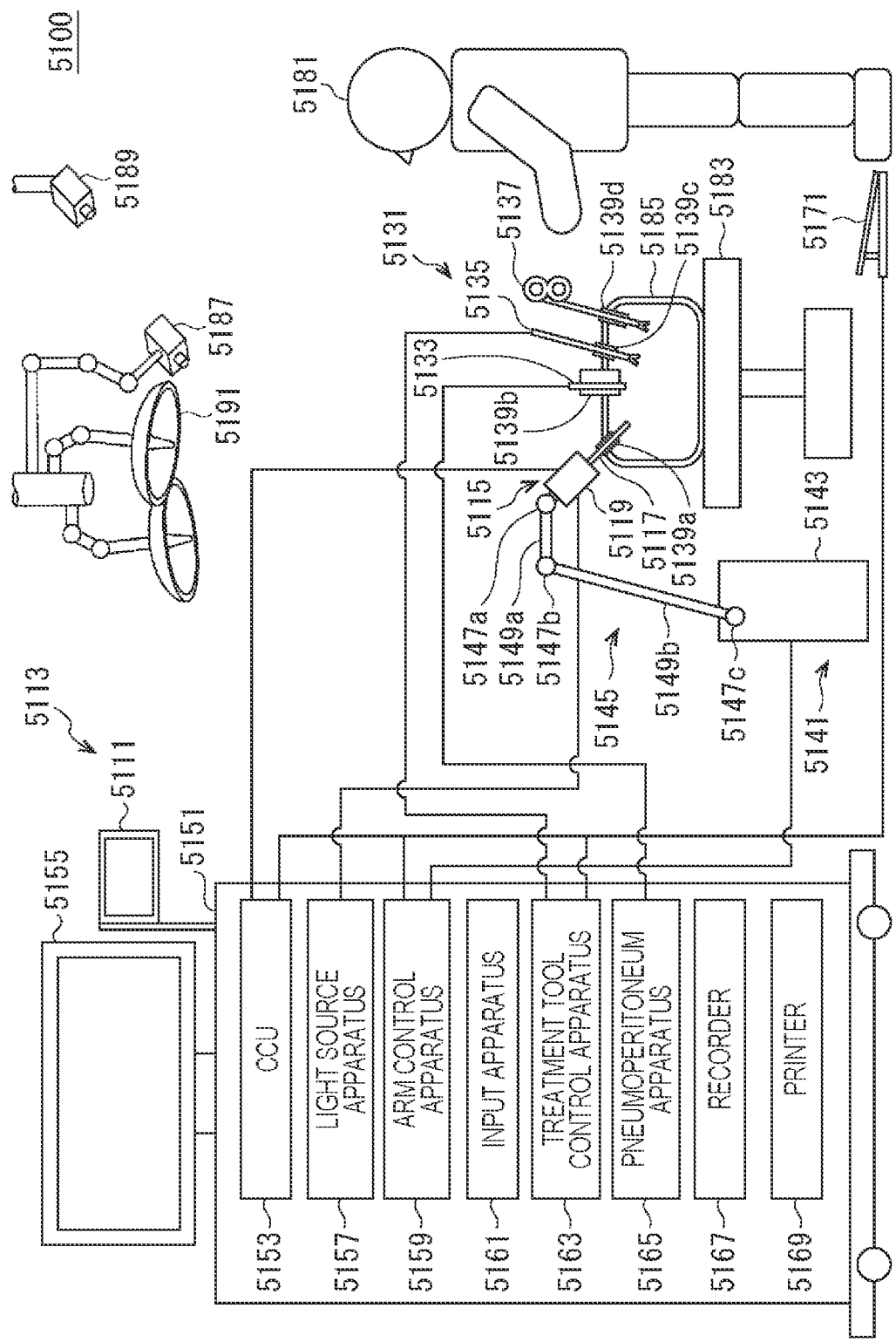
FIG. 14 is a diagram showing an example of a state of a surgery to which the surgery room system is applied.

As shown in FIG. 12, the endoscope surgery system 5113, the patient bed 5183, the ceiling camera 5187, the surgery site camera 5189, and the illumination 5191 are connected to be capable of cooperating with each other, through the audiovisual controller 5107 and the surgery room control apparatus 5109 (not shown in FIG. 14). In the surgery room, the centralized manipulation panel 5111 is provided, and as described above, the user is capable of suitably manipulating these apparatuses existing in the surgery room, through the centralized manipulation panel 5111.

Hereinafter, the configuration of the endoscope surgery system 5113 will be described in detail. As shown in the drawing, the endoscope surgery system 5113 includes an endoscope 5115, other surgical tools 5131, a support arm apparatus 5141 supporting the endoscope 5115, and a cart 5151 on which various apparatuses for an endoscopic surgery are mounted.

In the endoscope surgery, a plurality of tubular perforating tools referred to as trocars 5139a to 5139d, is punctured on an abdominal wall, instead of performing laparotomy by cutting the abdominal wall. Then, a lens tube 5117 of the endoscope 5115, and the other surgical tools 5131 are inserted into the body cavity of the patient 5185, from the trocars 5139a to 5139d. In the shown example, as the other surgical tools 5131, a pneumoperitoneum tube 5133, an energy treatment tool 5135, and forceps 5137 are inserted into the body cavity of the patient 5185. Furthermore, the energy treatment tool 5135 is a treatment tool performing incision and ablation of a tissue, sealing of a blood vessel, and the like, by a high frequency current or an ultrasonic vibration. Here, the shown surgical tool 5131 is merely an example, and for example, various surgical tools generally used in the endoscopic surgery, such as tweezers and a retractor, may be used as the surgical tool 5131.

The image of the surgery portion in the body cavity of the patient 5185, captured by the endoscope 5115, is displayed on the display apparatus 5155. The surgery operator 5181, for example, performs a treatment such as excision of the affected part by using the energy treatment tool 5135 or the forceps 5137, while observing the image of the surgery portion displayed on the display apparatus 5155 in real time. Note that, even though it is not shown in the drawing, the pneumoperitoneum tube 5133, the energy treatment tool 5135, and the forceps 5137 are supported by the surgery operator 5181, an assistant, or the like, during the surgery.

(Support Arm Apparatus)

The support arm apparatus 5141 includes an arm portion 5145 extending from a base portion 5143. In the shown example, the arm portion 5145 includes joint portions 5147a, 5147b, and 5147c, and links 5149a and 5149b, and is driven according to the control from the arm control apparatus 5159. The endoscope 5115 is supported by the arm portion 5145, and the position and the posture thereof are controlled. Therefore, a stable position of the endoscope 5115 can be fixed.

(Endoscope)

The endoscope 5115 includes a lens tube 5117 in which an area of a predetermined length from a tip end, is inserted into the body cavity of the patient 5185, and a camera head 5119 connected to a base end of the lens tube 5117. In the shown example, the endoscope 5115 configured as a so-called rigid scope including a rigid lens tube 5117, is shown, but the endoscope 5115 may be configured as a so-called flexible scope including a flexible lens tube 5117.

An opening portion into which an objective lens is fitted, is provided at the tip end of the lens tube 5117. A light source apparatus 5157 is connected to the endoscope 5115, and light generated by the light source apparatus 5157 is guided to the tip end of the lens tube by a light guide provided to extend in the lens tube 5117, and is applied towards an observation target in the body cavity of the patient 5185 through the objective lens. Note that the endoscope 5115 may be a forward-viewing endoscope, or may be an oblique-viewing endoscope or a side-viewing endoscope.

In the camera head 5119, an optical system and an imaging element are provided, and reflection light (observation light) from the observation target, is condensed in the imaging element by the optical system. The observation light is subjected to the photoelectric conversion by the imaging element, and an electrical signal corresponding to the observation light, that is, an image signal corresponding to an observation image, is generated. The image signal is transmitted to a camera control unit (CCU) 5153, as RAW data. Note that in the camera head 5119, a function of adjusting a magnification and a focal point distance by suitably driving the optical system, is provided.

Note that, for example, a plurality of imaging elements may be provided in the camera head 5119, in order to correspond to a stereoscopic view (3D display) or the like. In this case, a plurality of relay optical systems is provided in the lens tube 5117, in order to guide the observation light to each of the plurality of imaging elements.

(Various Apparatuses Mounted on Cart)

The CCU 5153 includes a central processing unit (CPU), a graphics processing unit (GPU), or the like, and integrally controls the operation of the endoscope 5115 and the display apparatus 5155. Specifically, the CCU 5153 performs, on the image signal received from the camera head 5119, various image processing for displaying the image based on the image signal, such as development processing (demosaic processing), for example. The CCU 5153 provides the image signal subjected to the image processing, to the display apparatus 5155. Furthermore, the audiovisual controller 5107 shown in FIG. 12, is connected to the CCU 5153. The CCU 5153 also provides the image signal subjected to the image processing, to the audiovisual controller 5107. Furthermore, the CCU 5153 transmits a control signal to the camera head 5119, and controls the driving thereof. The control signal is capable of including information associated with an imaging condition such as a magnification or a focal point distance. The information associated with the imaging condition may be input through an input apparatus 5161, or may be input through the centralized manipulation panel 5111 described above.

The display apparatus 5155 displays an image based on the image signal subjected to the image processing by the CCU 5153, according to the control from the CCU 5153. In a case where the endoscope 5115, for example, corresponds to high-definition capturing such as 4K (the number of horizontal pixels of 3840×the number of vertical pixels of 2160) or 8K (the number of horizontal pixels of 7680×the number of vertical pixels of 4320), and/or corresponds to 3D display, a display apparatus capable of performing high-definition display corresponding to each of 4K and 8K, and/or a display apparatus capable of performing 3D display, can be used as the display apparatus 5155. In the case of corresponding to the high-definition capturing such as 4K or 8K, a display apparatus having a size of greater than or equal to 55 inches is used as the display apparatus 5155, and thus, more immersion feeling can be obtained. Furthermore, a plurality of display apparatuses 5155 having different definitions and sizes may be provided, according to a use application.

The light source apparatus 5157, for example, includes a light source such as a light emitting diode (LED), and supplies the irradiation light at the time of capturing the surgery portion, to the endoscope 5115.

The arm control apparatus 5159, for example, includes a processor such as a CPU, and is operated according to a predetermined program, and thus, controls the driving of the arm portion 5145 of the support arm apparatus 5141, according to a predetermined control method.

The input apparatus 5161 is an input interface with respect to the endoscope surgery system 5113. The user is capable of performing the input of various information, or the input of an instruction with respect to endoscope surgery system 5113, through the input apparatus 5161. For example, the user inputs various information associated with the surgery, such as the body information of the patient, and the information associated with the surgery method of the surgery, through the input apparatus 5161. Furthermore, for example, the user inputs an instruction of driving the arm portion 5145, an instruction of changing the imaging condition of the endoscope 5115 (the type of irradiation light, the magnification, the focal point distance, and the like), an instruction of driving the energy treatment tool 5135, and the like, through the input apparatus 5161.

The type of input apparatus 5161 is not limited, and the input apparatus 5161 may be various known input apparatuses. For example, a mouse, a keyboard, a touch panel, a switch, a foot switch 5171 a lever, and/or the like can be applied as the input apparatus 5161. In a case where the touch panel is used as the input apparatus 5161, the touch panel may be disposed on the display surface of the display apparatus 5155.

Alternatively, the input apparatus 5161, for example, is a device mounted on the user, such as a glasses type wearable device or a head mounted display (HMD), and various inputs are performed according to the gesture or a line-of-sight of the user, which is detected by such a device. Furthermore, the input apparatus 5161 includes a camera capable of detecting the motion of the user, and various inputs are performed according to the gesture or the line-of-sight of the user detected from a video captured by the camera. Moreover, the input apparatus 5161 includes a microphone capable of picking up the voice of the user, and various inputs are performed according to the sound through the microphone. The input apparatus 5161 is configured as described above such that various information can be input in a non-contact manner, and thus, in particular, a user belonging to a clean area (for example, the surgery operator 5181) is capable of manipulating the equipment belonging to an unclean area, in a non-contact manner. Furthermore, the user is capable of manipulating the equipment without releasing the hands from the possessed surgical tool, and thus, convenience of the user is improved.

The treatment tool control apparatus 5163 controls the driving of the energy treatment tool 5135 for the cauterization and the incision of the tissue, the sealing of the blood vessel, or the like. In order to ensure a visual field of the endoscope 5115 and to ensure a working space of the surgery operator, the pneumoperitoneum apparatus 5165 sends gas into the body cavity through the pneumoperitoneum tube 5133 such that the body cavity of the patient 5185 is inflated. The recorder 5167 is an apparatus capable of recording various information associated with the surgery. The printer 5169 is an apparatus capable of printing various information associated with the surgery, in various formats such as a text, an image, or a graph.

Hereinafter, in the endoscope surgery system 5113, a particularly characteristic configuration will be described in more detail.

(Support Arm Apparatus)

The support arm apparatus 5141 includes the base portion 5143 which is a base, and the arm portion 5145 extending from the base portion 5143. In the shown example, the arm portion 5145 includes the plurality of joint portions 5147a, 5147b, and 5147c, and the plurality of links 5149a and 5149b joined by the joint portion 5147b, but in FIG. 14, for the sake of simplicity, the configuration of the arm portion 5145 is simply shown. Actually, the shape of the joint portions 5147a to 5147c and the links 5149a and 5149b, the number of joint portions 5147a to 5147c and links 5149a and 5149b, the arrangement of the joint portions 5147a to 5147c and the links 5149a and 5149b, a rotation axis direction of the joint portions 5147a to 5147c, and the like are suitably set such that the arm portion 5145 has a desired freedom degree. For example, the arm portion 5145 can preferably have a freedom degree of greater than or equal to six. Therefore, the endoscope 5115 can be freely moved within a movement range of the arm portion 5145, and thus, it is possible to insert the lens tube 5117 of the endoscope 5115 into the body cavity of the patient 5185 from a desired direction.

In the joint portions 5147a to 5147c, an actuator is provided, and the joint portions 5147a to 5147c can be rotated around a predetermined rotation axis by driving the actuator. The driving of the actuator is controlled by the arm control apparatus 5159, and thus, a rotation angle of each of the joint portions 5147a to 5147c is controlled, and the driving of the arm portion 5145 is controlled. Therefore, the position and the posture of the endoscope 5115 can be controlled. At this time, the arm control apparatus 5159 is capable of controlling the driving of the arm portion 5145, according to various known control methods such as force control or position control.

For example, the surgery operator 5181 performs suitable manipulation input through the input apparatus 5161 (including the foot switch 5171), and thus, the driving of the arm portion 5145 may be suitably controlled by the arm control apparatus 5159, according to the manipulation input, and the position and the posture of the endoscope 5115 may be controlled. According to the control, the endoscope 5115 at the tip end of the arm portion 5145 can be moved to an arbitrary position from an arbitrary position, and then, can be fixedly supported in the position after the movement. Note that the arm portion 5145 may be manipulated by a so-called master-slave system. In this case, the arm portion 5145 can be remotely manipulated by the user, through the input apparatus 5161 provided in a location apart from the surgery room.

Furthermore, in a case where the force control is applied, so-called power assist control may be performed, in which the arm control apparatus 5159 receives an external force from the user, and drives the actuator of each of the joint portions 5147a to 5147c such that the arm portion 5145 is smoothly moved according to the external force. Therefore, when the user moves the arm portion 5145 while directly touching the arm portion 5145, it is possible to move the arm portion 5145 with a comparatively light force. Accordingly, it is possible to more intuitively move the endoscope 5115 by a simpler manipulation, and to improve the convenience of the user.

Here, in general, in the endoscopic surgery, the endoscope 5115 is supported by a medical doctor referred to as a scopist. In contrast, the position of the endoscope 5115 can be more reliably fixed by using the support arm apparatus 5141, without manual work, and thus, it is possible to stably obtain the image of the surgery portion, and to smoothly perform the surgery.

Note that the arm control apparatus 5159 may not be necessarily provided in the cart 5151. Furthermore, the arm control apparatus 5159 may not be necessarily one apparatus. For example, the arm control apparatus 5159 may be provided in each of the joint portions 5147a to 5147c of the arm portion 5145 of the support arm apparatus 5141, and a plurality of arm control apparatuses 5159 may cooperate with each other, and thus, the driving control of the arm portion 5145 may be realized.

(Light Source Apparatus)

The light source apparatus 5157 supplies the irradiation light at the time of capturing the surgery portion, to the endoscope 5115. The light source apparatus 5157 includes a white light source including, for example, an LED, a laser light source, or a combination thereof. At this time, in a case where the white light source includes a combination of RGB laser light sources, it is possible to control an output intensity and an output timing of each color (each wavelength) with a high accuracy, and thus, it is possible to adjust a white balance of the captured image in the light source apparatus 5157. Furthermore, in this case, laser light from each of the RGB laser light sources is applied to the observation target in time division, and the driving of the imaging element of the camera head 5119 is controlled in synchronization with the irradiation timing, and thus, it is also possible to capture an image corresponding to each of RGB in time division.

According to such a method, it is possible to obtain a color image without providing a color filter in the imaging element.

Furthermore, the driving of the light source apparatus 5157 may be controlled such that the intensity of the light to be output is changed for each predetermined time. The driving of the imaging element of the camera head 5119 is controlled in synchronization with a timing when the intensity of the light is changed to acquire images in a time division manner, and the images are combined It is thus possible to generate an image of a high dynamic range, without so-called black defects and overexposure.

Furthermore, the light source apparatus 5157 may be configured to supply light of a predetermined wavelength band corresponding to special light imaging. In the special light imaging, for example, light with a narrower band is applied, compared to irradiation light at the time of performing usual observation by using wavelength dependency of absorbing light in the body tissue (i.e., white light), and thus, so-called narrow band imaging of capturing a predetermined tissue of a blood vessel or the like in a superficial portion of a mucous membrane with a high contrast, is performed. Alternatively, in the special light imaging, fluorescent light imaging of obtaining an image by fluorescent light generated by being irradiated with excited light, may be performed. In the fluorescent light imaging, for example, the body tissue is irradiated with the excited light, and the fluorescent light from the body tissue is observed (autofluorescent light imaging), or a reagent such as indocyanine green (ICG) is locally injected into the body tissue, and the body tissue is irradiated with excited light corresponding to a fluorescent light wavelength of the reagent, and thus, a fluorescent image is obtained. The light source apparatus 5157 can be configured to supply the narrow band light and/or the excited light corresponding to such special light imaging.

(Camera Head and CCU)

Figure 15:
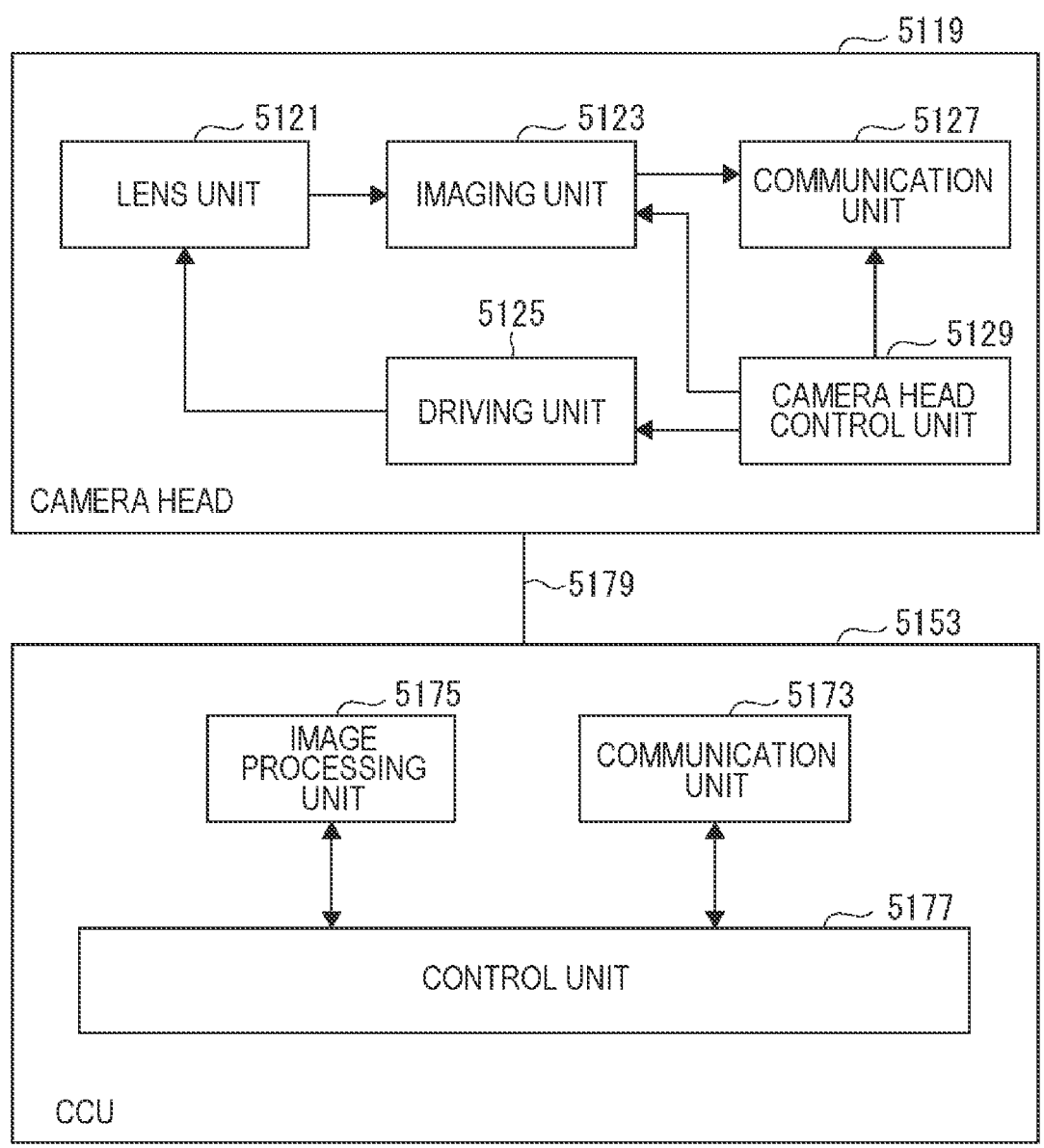
FIG. 15 is a block diagram showing an example of a functional configuration of a camera head and a CCU shown in FIG. 14.

The function of the camera head 5119 and the CCU 5153 of the endoscope 5115 will be described in more detail, with reference to FIG. 15. FIG. 15 is a block diagram showing an example of a functional configuration of the camera head 5119 and the CCU 5153 shown in FIG. 14.

With reference to FIG. 15, the camera head 5119 includes a lens unit 5121, an imaging unit 5123, a driving unit 5125, a communication unit 5127, and a camera head control unit 5129, as the function thereof. Furthermore, the CCU 5153 includes a communication unit 5173, an image processing unit 5175, and a control unit 5177, as the function thereof. The camera head 5119 and the CCU 5153 are connected to be capable of bidirectionally communicating with each other through a transmission cable 5179.

First, the functional configuration of the camera head 5119 will be described. The lens unit 5121 is an optical system provided in a connection portion with the lens tube 5117. Observation light incorporated from a tip end of the lens tube 5117, is guided to the camera head 5119, and is incident on the lens unit 5121. The lens unit 5121 includes a combination of a plurality of lenses including a zoom lens and a focus lens. Optical characteristics of the lens unit 5121 are adjusted such that the observation light is condensed on a light receiving surface of an imaging element of the imaging unit 5123. Furthermore, the zoom lens and the focus lens are configured such that the positions of the zoom lens and the focus lens on an optical axis can be moved in order to adjust the magnification and a focal point of the captured image.

The imaging unit 5123 includes an imaging element, and is arranged on the later stage of the lens unit 5121. The observation light passing through the lens unit 5121, is condensed on the light receiving surface of the imaging element, and an image signal corresponding to the observation image is generated by the photoelectric conversion. The image signal generated by the imaging unit 5123, is provided to the communication unit 5127.

For example, a complementary metal oxide semiconductor (CMOS) type image sensor, which is capable of performing color capturing having a Bayer array, is used as the imaging element configuring the imaging unit 5123. Note that, for example, an element capable of corresponding to high-definition image capturing of greater than or equal to 4K, may be used as the imaging element. The image of the surgery portion is obtained with a high definition, and thus, the surgery operator 5181 is capable of more specifically grasping the state of the surgery portion, and the surgery can be progressed more smoothly.

Furthermore, the imaging element configuring the imaging unit 5123 includes a pair of imaging elements for acquiring each of an image signal for a right eye and an image signal for a left eye, corresponding to the 3D display. The 3D display is performed, and thus, the surgery operator 5181 is capable of more accurately grasping the depth of the biological tissue in the surgery portion. Note that, in a case where the imaging unit 5123 has a multi-plate type configuration, a plurality of lens units 5121 is provided corresponding to each of the imaging elements.

Furthermore, the imaging unit 5123 may not be necessarily provided in the camera head 5119. For example, the imaging unit 5123 may be provided immediately after the objective lens, in the lens tube 5117.

The driving unit 5125 includes an actuator, and moves the zoom lens and the focus lens of the lens unit 5121 along the optical axis by a predetermined distance, according to the control from the camera head control unit 5129. Therefore, it is possible to suitably adjust the magnification and the focal point of the image captured by the imaging unit 5123.

The communication unit 5127 includes a communication apparatus for transmitting and receiving various information with respect to the CCU 5153. The communication unit 5127 transmits the image signal obtained from the imaging unit 5123 to the CCU 5153 through the transmission cable 5179, as the RAW data. At this time, in order to display the captured image of the surgery portion with a low latency, it is preferable that the image signal be transmitted through optical communication. This is because at the time of the surgery, the surgery operator 5181 performs the surgery while observing the state of the affected part with the captured image, and thus, in order for a more secure and reliable surgery, a moving image of the surgery portion is required to be displayed in real time to the maximum extent. In a case where the optical communication is performed, in the communication unit 5127, a photoelectric conversion module converting an electrical signal into an optical signal, is provided. The image signal is converted into the optical signal by the photoelectric conversion module, and then, is transmitted to the CCU 5153 through the transmission cable 5179.

Furthermore, the communication unit 5127 receives a control signal for controlling the driving of the camera head 5119, from the CCU 5153. The control signal, for example, includes information associated with the imaging condition, such as information of designating a frame rate of the captured image, information of designating an exposure value at the time of the imaging, and/or information of designating the magnification and the focal point of the captured image. The communication unit 5127 provides the received control signal to the camera head control unit 5129. Note that the control signal from the CCU 5153 also may be transmitted through the optical communication. In this case, in the communication unit 5127, a photoelectric conversion module converting the optical signal into an electrical signal, is provided, and the control signal is converted into the electrical signal by the photoelectric conversion module, and then, is provided to the camera head control unit 5129.

Note that the imaging condition such as the frame rate, the exposure value, the magnification, and the focal point, described above, is automatically set by the control unit 5177 of the CCU 5153, on the basis of the acquired image signal. That is, a so-called auto exposure (AE) function, an auto focus (AF) function, and an auto white balance (AWB) function are provided in the endoscope 5115.

The camera head control unit 5129 controls the driving of the camera head 5119, on the basis of the control signal from the CCU 5153 received through the communication unit 5127. For example, the camera head control unit 5129 controls the driving of the imaging element of the imaging unit 5123, on the basis of the information of designating the frame rate of the captured image and/or the information of designating the exposure at the time of the imaging. Furthermore, for example, the camera head control unit 5129 suitably moves the zoom lens and the focus lens of the lens unit 5121 through the driving unit 5125, on the basis of the information of designating the magnification and the focal point of the captured image. Moreover, the camera head control unit 5129 may have a function of storing information for identifying the lens tube 5117 or the camera head 5119.

Note that the lens unit 5121, the imaging unit 5123, and the like are arranged in a sealed structure having high airtightness and waterproof properties, and thus, it is possible for the camera head 5119 to have resistance with respect to an autoclave sterilization treatment.

Next, the functional configuration of the CCU 5153 will be described. The communication unit 5173 includes a communication apparatus for transmitting and receiving various information with respect to the camera head 5119. The communication unit 5173 receives the image signal to be transmitted from the camera head 5119, through the transmission cable 5179. At this time, as described above, the image signal can be preferably transmitted through optical communication. In this case, in the communication unit 5173, a photoelectric conversion module converting an optical signal into an electrical signal, is provided corresponding to the optical communication. The communication unit 5173 provides the image signal converted into the electrical signal, to the image processing unit 5175.

Furthermore, the communication unit 5173 transmits the control signal for controlling the driving of the camera head 5119, to the camera head 5119. The control signal also may be transmitted through the optical communication.

The image processing unit 5175 performs various image processing on the image signal which is the RAW data transmitted from the camera head 5119. For example, various known signal processing such as development processing, high-image quality processing (band emphasizing processing, super-resolution processing, noise reduction (NR) processing and/or shake correction processing, or the like), and/or magnification processing (electron zoom processing), are included as the image processing. Furthermore, the image processing unit 5175 performs detection processing on the image signal, in order to perform AE, AF, and AWB.

The image processing unit 5175 includes a processor such as a CPU or a GPU, and the processor is operated according to a predetermined program, and thus, the image processing or the detection processing described above, can be performed. Note that, in a case where the image processing unit 5175 includes a plurality of GPUs, the image processing unit 5175 suitably divides information associated with the image signal, and performs the image processing in parallel, by the plurality of GPUs.

The control unit 5177 performs various controls relevant to the imaging of the surgery portion by the endoscope 5115, and the display of the captured image. For example, the control unit 5177 generates the control signal for controlling the driving of the camera head 5119. At this time, in a case where the imaging condition has been input by the user, the control unit 5177 generates the control signal on the basis of the input by the user. Alternatively, in a case where the AE function, the AF function, and the AWB function are provided in the endoscope 5115, the control unit 5177 suitably calculates an optimal exposure value, focal point distance, and white balance, according to the result of the detection processing by the image processing unit 5175, and generates the control signal.

Furthermore, the control unit 5177 displays the image of the surgery portion on the display apparatus 5155, on the basis of the image signal subjected to the image processing by the image processing unit 5175. At this time, the control unit 5177 recognizes various objects in the surgery portion image, by using various image recognition technologies. For example, the control unit 5177 detects the shape, the color, or the like of the edge of the object included in the surgery portion image, and thus, it is possible to recognize a surgical tool such as forceps, a specific biological portion, bleed, mist at the time of using the energy treatment tool 5135, and the like When the image of the surgery portion is displayed on the display apparatus 5155, the control unit 5177 displays various surgery support information to be superimposed on the image of the surgery portion, by using a recognition result. The surgery support information is displayed to be superimposed, and is presented to the surgery operator 5181, and thus, surgery can be progressed more securely and reliably.

The transmission cable 5179 connecting the camera head 5119 and the CCU 5153 together, is an electrical signal cable corresponding to the communication of the electrical signal, an optical fiber corresponding to the optical communication, or a composite cable thereof.

Here, in the shown example, the communication is performed in a wired manner, by using the transmission cable 5179, but the communication between the camera head 5119 and the CCU 5153, may be performed in a wireless manner. In a case where the communication between the camera head 5119 and the CCU 5153 is performed in a wireless manner, it is not necessary that the transmission cable 5179 is laid in the surgery room, and thus, a problem in which the movement of the medical staff in the surgery room is hindered by the transmission cable 5179 can be solved.

An example of the surgery room system 5100 to which the technology according to the present disclosure can be applied, has been described. Note that, here, a case where the medical system to which the surgery room system 5100 is applied, is the endoscope surgery system 5113, has been described as an example, but the configuration of the surgery room system 5100 is not limited to such an example. For example, the surgery room system 5100 may be applied to a flexible endoscope system for a test or a microscope surgery system, instead of the endoscope surgery system 5113.

The technique according to the present disclosure can be suitably applied to the IP converter apparatus (IPC) 5110 among the configurations described above. Specifically, as the IP converter apparatus (IPC) 5110, the IP converter reception apparatus 55 shown in FIGS. 3, 5, and 7 of the present disclosure can be preferably applied. By applying the technology according to the present disclosure to the IP converter apparatus (IPC) 5110, it is possible to suppress a reduction in resolution of an image that a surgery operator wants to see at a high resolution while responding to an increase in the number of connections of medical equipment that supply images.

Note that the present disclosure may adopt the configuration described below.

<1> A reception apparatus including:
   an acquisition unit that acquires an image from a plurality of pieces of equipment; and
   a plurality of compression units that compresses the image acquired by the acquisition unit by selecting a compression method for each type of the image.

<2> The reception apparatus according to <1>, in which the compression unit compresses the image acquired by the acquisition unit by selecting the compression method by performing bit packing by switching a bit packing method for each type of the image.

<3> The reception apparatus according to <2>, in which the compression unit compresses the image acquired by the acquisition unit by selecting the compression method by performing bit packing by switching the bit packing method by switching a format of a component signal for each type of the image.

<4> The reception apparatus according to <1>, in which the compression unit compresses the image acquired by the acquisition unit by selecting the compression method by switching a frame rate for each type of the image.

<5> The reception apparatus according to <1>, in which the compression unit compresses the image acquired by the acquisition unit by selecting the compression method by switching a compression rate according to an area of the image for each type of the image.

<6> The reception apparatus according to <1>, in which the compression unit compresses the image acquired by the acquisition unit by selecting the compression method by switching an encoding method for each type of the image.

<7> The reception apparatus according to <1>, in which
   the image includes a medical image, and
   the compression unit determines the type of the image on the basis of information object definition (IOD) data of digital imaging and communications in medicine (DICOM) attached to the image acquired by the acquisition unit.

<8> The reception apparatus according to <7>, in which a type of the medical image includes at least an operative field image, an endoscopic image, a laparoscopic image, a computed tomography (CT) image, a magnetic resonance imaging (MRI) image, or an X-ray image.

<9> The reception apparatus according to <1>, in which
   the image includes a medical image, and
   the compression unit determines the type of the image on the basis of an analysis result of the image acquired by the acquisition unit.

<10> The reception apparatus according to <9>, in which the compression unit determines the type of the image on the basis of an analysis result of a spatial frequency analysis or an analysis result of a dynamic range analysis of each channel of Y, Cb, and Cr signals in the image acquired by the acquisition unit.

<11> The reception apparatus according to <9>, in which the compression unit determines whether or not the type of the image is an endoscopic image on the basis of whether or not a round, black mask is present at a peripheral portion of the image in the analysis result of the image.

<12> The reception apparatus according to <9>, in which the compression unit determines whether or not the type of the image is either an X-image or a CT-image on the basis of whether or not the image is grayscale in the analysis of the image.

<13> The reception apparatus according to any of <1> to <12>, further including:
   a transmission unit that transmits a plurality of images compressed by the plurality of compression units;
   a generation unit that generates a single picture in picture (PinP) image by image processing that combines the plurality of images compressed by the plurality of compression units and transmitted by the transmission unit; and
   an output unit that outputs the single picture in picture (PinP) image to a display unit via the transmission unit and causes the display unit to display the single PinP image.

<14> The reception apparatus according to <13>, in which the compression unit compresses the image acquired by the acquisition unit by selecting a compression method for each type of the image by switching a bit packing format according to a processing load of a processor of the generation unit.

<15> The reception apparatus according to <14>, in which the compression unit performs compression by selecting the compression method by switching the bit packing format to either a format with a first compression rate including a format other than 16-bit alignment or a format with a second compression rate having a compression rate lower than the first compression rate including the format of the 16-bit alignment according to the processing load of the processor of the generation unit.

<16> The reception apparatus according to <15>, in which the compression unit performs compression
   by selecting the compression method by switching the bit packing format to the format with the first compression rate including the format other than the 16-bit alignment when the processing load of the processor of the generation unit is smaller than a predetermined value and by switching the bit packing format to the format with the second compression rate having a compression rate lower than the first compression rate including the format of the 16-bit alignment when the processing load of the processor of the generation unit is larger than the predetermined value.

<17> The reception apparatus according to <13>, in which the transmission unit includes peripheral component interconnect express (PCIe).

<18> The reception apparatus according to <13>, in which the compression unit performs compression by selecting the compression method according to a display function of the display unit in a case where the image includes a 3D compatible image.

<19> A reception method including:
   acquisition processing of acquiring an image from a plurality of pieces of equipment; and
   compression processing of compressing the image acquired by the acquisition processing by selecting a compression method for each type of the image.

<20> An image processing system including:
an image server that stores an image from a plurality of pieces of equipment; and
a reception apparatus that acquires an image from the image server, outputs the image to a display unit, and causes the display unit to display the image,
in which
the image server stores an image from the plurality of pieces of equipment and includes an output unit that outputs the stored image to the reception apparatus, and
the reception apparatus includes
an acquisition unit that acquires the image from the plurality of pieces of equipment from the image server and
a plurality of compression units that compresses the image acquired by the acquisition unit by selecting a compression method for each type of the image.

REFERENCE SIGNS LIST

11 IP converter reception apparatus (IPC-Rx)
31 Input unit (Network Rx)
32, 32-1 to 32-n Decoder
33 Expansion bus (peripheral component interconnect express (PCIe))
34 Graphics processing unit (GPU)
35 Output unit (serial digital interface (SDI))
40 Intra-hospital image processing system
50 Camera
51 Camera control unit (CCU)
52 IP converter transmission apparatus (IPC-Tx)
71 Input unit (Network Rx)
72, 72-1 to 72-n Decoder
73, 73-1 to 73-n Bit packing unit (BitPack)
74 Bit packing control unit (PackingCtrl)
75 Table
76 Expansion bus (peripheral component interconnect express (PCIe))
77 Graphics processing unit (GPU)
78 Output unit (serial digital interface (SDI))
91, 91-1 to 91-n Encoder (Enc)
92 Table
93 Graphics processing unit (GPU)
111, 111-1 to 111-n Decoder (Dec)
131, 131-1 to 131-n Bit packing unit (BitPack)
132 Bit packing control unit (PackingCtrl)
133 GPU
151 Processor

The invention claimed is:

1. A reception apparatus, comprising:
an acquisition unit configured to acquire an image from a plurality of pieces of equipment; and
a compression unit configured to:
select a bit packing method based on a type of the image, wherein the bit packing method is based on a format of a component signal for the type of the image; and
compress the image by bit packing, wherein the bit packing is based on the selected bit packing method.

2. The reception apparatus according to claim 1, wherein the image includes a medical image, and
the compression unit is further configured to determine the type of the image based on an information object definition (IOD) data of digital imaging and communications in medicine (DICOM) attached to the image acquired by the acquisition unit.

3. The reception apparatus according to claim 2, wherein the type of the medical image includes at least an operative field image, an endoscopic image, a laparoscopic image, a computed tomography (CT) image, a magnetic resonance imaging (MRI) image, or an X-ray image.

4. The reception apparatus according to claim 1, wherein the image includes a medical image, and
the compression unit is further configured to determine the type of the image based on an analysis result of the image acquired by the acquisition unit.

5. The reception apparatus according to claim 4, wherein the compression unit is further configured to determine the type of the image based on an analysis result of a spatial frequency analysis or an analysis result of a dynamic range analysis of each channel of Y, Cb, and Cr signals in the image acquired by the acquisition unit.

6. The reception apparatus according to claim 4, wherein the compression unit is further configured to determine whether the type of the image is an endoscopic image based on whether a round, black mask is present at a peripheral portion of the image in the analysis result of the image.

7. The reception apparatus according to claim 4, wherein the compression unit is further configured to determine whether the type of the image is either an X-image or a CT-image based on whether the image is grayscale in the analysis result of the image.

8. The reception apparatus according to claim 1, further comprising:
a transmission unit configured to transmit a plurality of images compressed by a plurality of compression units;
a generation unit configured to generate a single picture in picture (PinP) image by image processing that combines the plurality of images compressed by the plurality of compression units and transmitted by the transmission unit; and
an output unit configured to:
output the single PinP image to a display unit via the transmission unit; and
cause the display unit to display the single PinP image.

9. The reception apparatus according to claim 8, wherein the compression unit is further configured to compress the image by selecting a compression method for the type of the image by switching a bit packing format according to a processing load of a processor of the generation unit.

10. The reception apparatus according to claim 9, wherein the compression unit is further configured to perform compression by selecting the compression method by switching the bit packing format to either a format with a first compression rate including a format other than 16-bit alignment or a format with a second compression rate having a compression rate lower than the first compression rate including a format of the 16-bit alignment according to the processing load of the processor of the generation unit.

11. The reception apparatus according to claim 10, wherein the compression unit is further configured to perform compression
by selecting the compression method by switching the bit packing format to the format with the first compression rate including the format other than the 16-bit alignment when the processing load of the processor of the generation unit is smaller than a specific value; and
by switching the bit packing format to the format with the second compression rate having a compression rate lower than the first compression rate including the format of the 16-bit alignment when the processing load of the processor of the generation unit is larger than the specific value.

12. The reception apparatus according to claim 8, wherein the transmission unit includes peripheral component interconnect express (PCIe).

13. The reception apparatus according to claim 8, wherein the compression unit is configured to perform compression by selecting a compression method according to a display function of the display unit in a case where the image includes a 3D compatible image.

14. A reception method, comprising:
acquiring an image from a plurality of pieces of equipment;
selecting a bit packing method based on a type of the image, wherein the bit packing method is based on a format of a component signal for the type of the image; and
compressing the image by bit packing, wherein the bit packing is based on the selected bit packing method.

15. An image processing system, comprising:
an image server configured to store an image from a plurality of pieces of equipment; and
a reception apparatus configured to:
acquire the image from the image server;
output the image to a display unit; and
cause the display unit to display the image, wherein
the image server is configured to store the image from the plurality of pieces of equipment and includes an output unit that outputs the stored image to the reception apparatus, and
the reception apparatus includes:
an acquisition unit configured to acquire the image from the plurality of pieces of equipment from the image server and
a compression unit configured to:
select a bit packing method based on a type of the image, wherein the bit packing method is based on a format of a component signal for the type of the image; and
compress the image by bit packing, wherein the bit packing is based on the selected bit packing method.

16. A reception apparatus, comprising:
an acquisition unit configured to acquire an image from a plurality of pieces of equipment;
a plurality of compression units configured to compress the image acquired by the acquisition unit by selecting a compression method for a type of the image;
a transmission unit configured to transmit a plurality of images compressed by the plurality of compression units;
a generation unit configured to generate a single picture in picture (PinP) image by image processing that combines the plurality of images compressed by the plurality of compression units and transmitted by the transmission unit; and
an output unit configured to:
output the single PinP image to a display unit via the transmission unit; and
cause the display unit to display the single PinP image.

* * * * *